United States Patent
Timmis et al.

(10) Patent No.: US 8,744,775 B2
(45) Date of Patent: Jun. 3, 2014

(54) METHODS FOR CLASSIFICATION OF SOMATIC EMBRYOS COMPRISING HYPERSPECTRAL LINE IMAGING

(75) Inventors: Roger Timmis, Olympia, WA (US); Paul R. Spencer, Pullman, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 1042 days.

(21) Appl. No.: 12/317,560

(22) Filed: Dec. 23, 2008

(65) Prior Publication Data

US 2009/0171591 A1    Jul. 2, 2009

Related U.S. Application Data

(60) Provisional application No. 61/009,431, filed on Dec. 28, 2007.

(51) Int. Cl.
    *G01N 33/48*      (2006.01)

(52) U.S. Cl.
    USPC .......................................................... 702/19

(58) Field of Classification Search
    USPC .......................................................... 702/19
    See application file for complete search history.

(56) References Cited

U.S. PATENT DOCUMENTS

| | | | |
|---|---|---|---|
| 5,036,007 A | 7/1991 | Gupta | |
| 5,236,841 A | 8/1993 | Gupta | |
| 5,464,769 A | 11/1995 | Attree | |
| 5,563,061 A | 10/1996 | Gupta | |
| 5,590,261 A | 12/1996 | Sclaroff | |
| 5,638,284 A | 6/1997 | Helmer | |
| 5,680,320 A | 10/1997 | Helmer | |
| 5,680,321 A | 10/1997 | Helmer | |
| 5,710,833 A | 1/1998 | Moghaddam | |
| 5,808,303 A | 9/1998 | Schlagheck | |
| 5,842,150 A | 11/1998 | Renberg | |
| 6,563,653 B2 | 5/2003 | Ramm | |
| 7,298,415 B2 | 11/2007 | Nilson | |
| 2003/0060693 A1 | 3/2003 | Monfre | |
| 2004/0003426 A1 | 1/2004 | Gupta | |
| 2004/0224301 A1* | 11/2004 | Timmis et al. | 702/19 |
| 2006/0082762 A1 | 4/2006 | Leverette | |
| 2006/0247514 A1 | 11/2006 | Panasyuk | |
| 2006/0280216 A1 | 12/2006 | Jayaraman | |
| 2007/0276640 A1 | 11/2007 | Timmis | |

OTHER PUBLICATIONS

Mills et al. (Journal of Cereal Science, vol. 41, 2005, p. 193-201).*
Lestander (Doctoral Thesis, Swedish University of Agricultural Sciences, Umeå, 63 pages, 2003).*
Cheng, Z., and P.P. Ling, "Machine vision techniques for somatic coffee embryo morphological feature extraction," Trans. Amer. Soc. Agri. Eng. 37:1663 1669 (1994).
Chi, C.M., C. Zhang, E.J. Staba, T.J. Cooke, and W S. Hu, "An advanced image analysis system for evaluation of somatic embryo development," Biotech. and Bioeng. 50:65 72 (1996).
Chanprame, S., T.M. Kuo, and J.M. Widholm, "Soluble carbohydrate content of soybean [*Gycine max* (L.) Merr.] somatic and zygotic embryos during development," In Vitro Cell Dev. Biol-Plant. 34:64 68 (1998).
Dodeman, V.L., M. Le Guilloux, G. Ducreux, and D. de Vienne, "Somatic and zygotic embryos of *Daucus carota* L. display different protein patterns until conversion to plants," Plant Cell Physiol. 39:1104 1110 (1998).
Morcillo, F., F. Aberlenc Bertossi, S. Hamon, and Y. Duval, "Accumulation of storage protein and 7S globulins during zygotic and somatic embryo development in Elaeis guineensis," Plant Physiol. Biochem. 36:509 514 (1998).
Obendorf, R.L., A.M. Dickerman, T.M. Pflum, M.A. Kacalanos, and M.E. Smith, "Drying rate alters soluble carbohydrates, desiccation tolerance, and subsequent seedling growth of soybean (*Glycine mac* L. Merrill) zygotic embryos during in vitro maturation," Plant Sci. 132:1 12 (1998).

* cited by examiner

*Primary Examiner* — Jerry Lin
(74) *Attorney, Agent, or Firm* — Baker Hostetler LLP

(57) ABSTRACT

The present invention relates to methods, apparatus, and imaging systems for using near-infrared spectroscopy imaging of plant embryos for classifying plant embryos. In one embodiment, a method is provided for classifying a plant embryo of an unknown type based on near infrared spectroscopy imaging.

13 Claims, 18 Drawing Sheets

(12 of 18 Drawing Sheet(s) Filed in Color)

METHODS FOR CLASSIFICATION OF SOMATIC EMBRYOS COMPRISING HYPERSPECTRAL LINE IMAGING

CROSS-REFERENCE TO RELATED APPLICATION

This application claims the benefit of U.S. Provisional Application No. 61/009,431, filed Dec. 28, 2007, which is hereby incorporated by reference.

BACKGROUND

Reproduction of selected plant varieties by tissue culture has been a commercial success for many years. The technique has enabled mass production of genetically identical selected ornamental plants, agricultural plants, and forest species. The woody plants in this last group have perhaps posed the greatest challenges. Some success with conifers was achieved in the 1970s using organogenesis techniques wherein a bud, or other organ, was placed on a culture medium where it was ultimately replicated many times. The newly generated buds were placed on a different medium that induced root development. From there, the buds having roots were planted in soil.

While conifer organogenesis was a breakthrough, costs were high due to the large amount of handling needed. There was also some concern about possible genetic modification. It was a decade later before somatic embryogenesis achieved a sufficient success rate so as to become the predominant approach to conifer tissue culture. With somatic embryogenesis, an explant, usually a seed or seed embryo, is placed on an initiation medium where it multiplies into a multitude of genetically identical immature embryos. These can be held in culture for long periods and multiplied to bulk up a particularly desirable clone. Ultimately, the immature embryos are placed on a development or maturation medium where they grow into somatic analogs of mature seed embryos. These embryos are then individually selected and placed on a germination medium for further development. Alternatively, the embryos may be used in manufactured seeds.

There is now a large body of general technical literature and a growing body of patent literature on embryogenesis of plants. Examples of procedures for conifer tissue culture are found in U.S. Pat. Nos. 5,036,007 and 5,236,841, issued to Gupta et al.; U.S. Pat. No. 5,183,757, issued to Roberts; U.S. Pat. No. 5,464,769, issued to Attree et al.; and U.S. Pat. No. 5,563,061, issued to Gupta.

One of the more labor intensive and subjective steps in the embryogenesis procedure is the selection from the maturation medium of individual embryos suitable for germination. The embryos may be present in a number of stages of maturity and development. Those that are most likely to successfully germinate into normal plants are preferentially selected using a number of visually evaluated screening criteria. Morphological features such as axial symmetry, cotyledon development, surface texture, color, and others are examined and applied as a pass/fail test before the embryos are passed on for germination. This is a skilled yet tedious job that is time consuming and expensive. Further, it poses a major production bottleneck when the ultimate desired output will be in the millions of plants.

It has been proposed to use some form of instrumental image analysis for embryo selection to replace the visual evaluation described above. For examples, refer to Cheng, Z., and P. P. Ling, "Machine vision techniques for somatic coffee embryo morphological feature extraction," Trans. Amer. Soc. Agri. Eng. 37:1663-1669 (1994), or Chi, C. M., C. Zhang, E. J. Staba, T. J. Cooke, and W-S. Hu, "An advanced image analysis system for evaluation of somatic embryo development," Biotech. and Bioeng 50:65-72 (1996). All of these methods require considerable pre-judgment of which morphological features are important and the development of mathematical methods to extract this information from the images. Relatively little of the information from the image has actually been used.

The problem of how to best use image analysis to automate the selection of somatic embryos after they had been separated from residual tissue, singulated, and imaged in color from multiple positions has not been successfully addressed. Various methods are known for extracting size and shape information from scanned images. As one example, Moghaddam et al., U.S. Pat. No. 5,710,833, describes a method useful for recognition of any multi-featured entity such as a human face. U.S. Pat. No. 5,590,261, issued to Sclaroff et al., describes a method that can be used for object recognition purposes.

Where embryos are concerned, a further problem using scanning technology is that morphology differs between clones within a given species. The differences between acceptable and rejected embryos can be very subtle, varying by clone. Hence, the choice of selection criteria for machine use tends to be subjective, difficult to specify mathematically, and may be clone specific.

The development of high-speed computers and new spectroscopic hardware has led to the development of new instruments which have the capability to rapidly acquire spectra on large numbers of samples. However, the acquisition of vast amounts of spectral data from a sample necessitates the development of similarly powerful data analysis tools to uncover subtle relationships between the collected spectra and the chemical properties of the sample. One such data analysis methodology, commonly known as chemometrics, applies multivariate statistical techniques to complex chemical systems in order to facilitate the discovery of the relationship between the absorption, transmittance or reflectance spectral data acquired from a sample and some specified property of the sample that is subject to independent measurement. The end result of multivariate analysis is the development of a predictive classification model that allows new samples of unknown properties to be rapidly and accurately classified according to a specified property based upon the acquired spectral data. For example, multivariate analysis techniques, such as: principal component analysis (PCA) and a principal component-based method, projection to latent structures (PLS), have been used to explore the multivariate information in previous applications of near-infrared (NIR) spectroscopy to the pulp and paper industry to develop classification models for paper quality. See, for example, U.S. Pat. Nos. 5,638,284, 5,680,320, 5,680,321, and 5,842,150.

Therefore, a continuing need exists for imaging systems and methods to capture spectral data from a biological sample and to use the collected spectra to develop classification models for the biological samples.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention relates to methods, devices, and systems for obtaining and using near-infrared imaging spectra for classification of plant embryos for determination of suitability for germination or other treatments.

In accordance with the foregoing, the present invention is based on a novel apparatus, system, and methods for classification of plant embryos by the application of classification algorithms to near-infrared (NIR) wavelength-by-position reflectance spectra of the plant embryos. The methods are generally applicable to various types of plant embryos and emphasize the importance of acquiring and using reflectance spectral information obtained from the embryos in combination with information on the position on the embryo from which the spectral information was obtained.

In one aspect of the invention, a method is provided for classifying plant embryos. The method comprises (a) developing a classification model by (i) acquiring reflectance spectral raw data from a plurality of positions along a desired axis of a plurality of embryo samples of a known embryo type; (ii) performing a data analysis by applying one or more classification algorithms to the spectral raw data, the data analysis resulting in development of a classification model for classifying plant embryos by embryo type; (b) acquiring reflectance spectral raw data from a plurality of positions along the corresponding axis of a plant embryo of unknown embryo type; and (c) applying the developed classification model to the spectral raw data of step (b) in order to classify the type of plant embryo of unknown embryo type.

In another aspect, the invention provides a method for classifying a plant embryo of an unknown type based on near infrared spectroscopy imaging. The method according to this aspect of the invention comprises (a) illuminating an axis of a plant embryo of unknown type; (b) capturing a hyperspectral line image from the light reflected off the illuminated plant embryo; (c) splitting the infrared portion of the captured line image into component wavelengths from 900 to 1680 nm; (d) detecting the split line image with a detector array; (e) outputting the detected image as wavelength-by-position data to at least one of a computer storage device, computer-readable media, or a user interface; and (f) comparing the wavelength-by-position data obtained from the axis of the embryo of unknown type to wavelength-by-position data of a reference plant embryo of known type to classify the plant embryo.

In another aspect, the invention provides a light diffusing sample chamber for capturing a hyperspectral line image of a living specimen. The light diffusing sample chamber comprises (i) a first circular housing defining an interior cone-shaped reflecting chamber, the first housing having an opening on the top at the widest part of the reflecting chamber for receiving a second circular housing, and having an opening at the bottom of the chamber for receiving a specimen; and (ii) a second circular housing defining an interior cone-shaped chamber, the second housing having a top opening at the widest part of the chamber for connection to an imaging apparatus, and a bottom opening at the narrow part of the chamber, wherein the second housing is mounted above the first housing and a portion of the chamber protrudes into the reflecting chamber.

In yet another aspect, the invention provides an imaging system for capturing reflectance spectral images from a living sample. The imaging system comprises an image sensor, a monochromator, an objective lens, and a light diffusing sample chamber for capturing a hyperspectral line image of a living specimen, the light diffusing sample chamber comprising: (i) a first circular housing defining an interior cone-shaped reflecting chamber, the first housing having an opening on the top at the widest part of the reflecting chamber for receiving a second circular housing, and having an opening at the bottom of the chamber for receiving a specimen; and (ii) a second circular housing defining an interior cone-shaped chamber, the second housing having a top opening at the widest part of the chamber for connection to an imaging apparatus, and a bottom opening at the narrow part of the chamber, wherein the second housing is mounted above the first housing and a portion of the chamber protrudes into the reflecting chamber.

The methods of the invention may be practiced using the apparatus and imaging system of the invention.

DESCRIPTION OF THE DRAWINGS

This patent or patent application file contains at least one drawing executed in color. Copies of this patent or patent application publication with color drawings will be provided by the U.S. Patent and Trademark Office upon request and payment of the necessary fee.

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
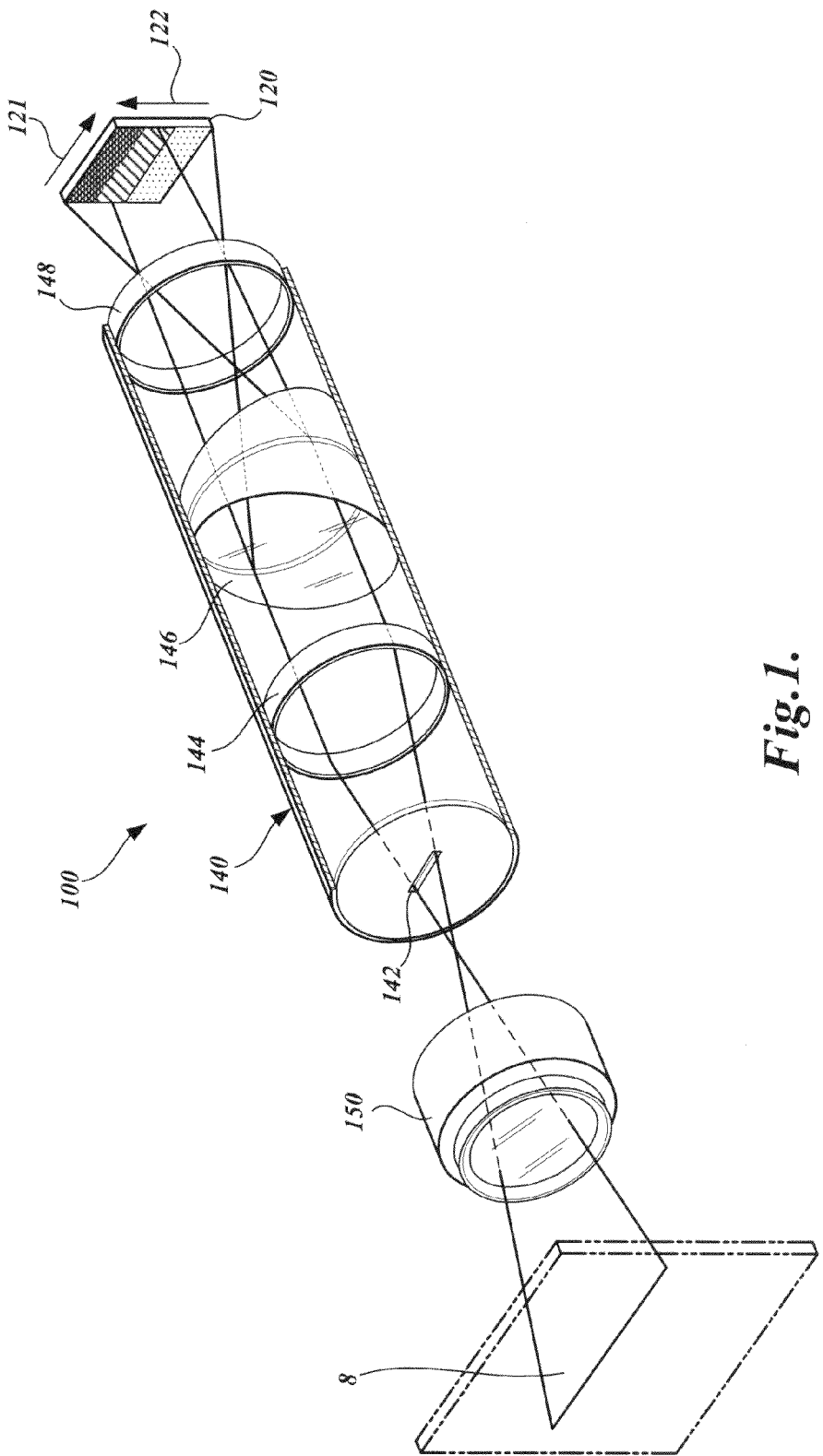
FIG. 1 is a schematic diagram showing a conventional system 100 for obtaining a hyperspectral line image in accordance with an embodiment of the methods of the invention.

The inventive apparatus, system and methods are used to classify any type of plant embryos, such as, for example, zygotic embryos, somatic embryos of various genotypes, or embryos with high or low conversion potential.

As used herein, "plant embryo type" refers to a group of plant embryos sharing at least one measurable feature that can serve as a basis for classification. Exemplary measurable features include at least one "plant embryo morphological feature" (e.g., axial symmetry, cotyledon development, surface texture, color, freedom from obvious flaws) as judged by visual analysis in comparison with a reference standard (such as a normal zygotic-like plant embryo), "plant embryo somatic genotype," and other "plant embryo qualities" (such as somatic plant embryo conversion potential, resistance to pathogens, drought resistance, heat or cold resistance, salt tolerance, preference for light quality, suitability for long-term storage of somatic embryos, response of embryos to certain culture protocols that may improve embryo production yield and/or vigor, or any other plant quality susceptible to quantification).

As used herein, "somatic plant embryo conversion potential" refers to the capacity of a somatic plant embryo to germinate and/or survive and grow in soil, preceded or not by desiccation or cold treatment of the embryo.

As used herein, a "pixel" is defined as the element of the detector array that collects and records the radiation on a particular area of the camera used for acquisition of the spectral data.

As used herein, the term "wavelength-by-position" refers to a spectrum of a single position along an axial line on the target (e.g., embryo). In some embodiments of the invention, the position corresponds to a single pixel-sized position along an axis of a target embryo. In some embodiments of the invention, the spectrum is an NIR spectrum.

Spectrometry is a well-known area of science that deals with the interaction of electromagnetic radiation with matter. These interactions with the energy states of chemical species include the reflectance, absorption, emission, and scattering of radiation. A spectrum is any display of the intensity of the radiation emitted, absorbed, reflected or scattered by the sample versus a measure of the energy of the radiation. From the information provided in a spectrum, details concerning the structure, function, and amount of a chemical species can be determined.

Near Infrared (NIR) Spectroscopy is a well-established analytical tool for the quantitative measurement of organic compounds. NIR spectroscopy can be used to non-destructively measure properties of living tissue with NIR energy in the 700 to 2500 nanometer wavelength range. The energy is focused onto an area of a living sample and propagates according to the scattering, absorption and reflectance properties of the sample. Therefore, the reflected or transmitted energy that escapes and is detected provides information about the portion of the sample that is encountered. The attenuation of the light energy at each wavelength is a function of the structural properties and chemical composition of the sample. Chemical components such as water, protein, fat, and analytes absorb light approximately proportionally to their concentration which are measured through unique absorption or reflectance profiles or signatures.

The measurement of properties of a living sample, such as a plant embryo, using NIR spectroscopy is based on detecting the magnitude of light attenuation resulting from its respective scattering, reflectance and/or absorption properties. By recording the pattern of light absorption (i.e., the absorption spectrum) in the wavelength region between 770 nm and 2500 nm, the amount and type of chemical bonds present in an unknown sample can be empirically determined. As with visible light imaging, NIR spectral analysis can be carried out in a macroscopic format to create true-sized images of samples. In diffuse reflectance mode, the light source is used to light a thick flat sample from the front, and light is collected that has diffused through the sample a small distance before being scattered back away from the sample surface onto the detector.

Spectral imaging refers to the technique of producing images based on chemical contrast that contains spectroscopic data at each pixel of the image. As described in co-pending U.S. patent application Ser. No. 11/836,095, incorporated herein by reference, methods are described for classifying embryos based on NIR spectral images obtained from plant embryos using only a circular field of view (e.g., 0.7 mm diameter), referred to as a "single patch" or "spot" analysis.

The use of an NIR-sensitive CCD camera 120 in conjunction with a monochromator 140 typically produces an array of 256×320 individual detectors to produce an 81,920 pixel two-dimensional image. In accordance with the methods of the present invention, it was experimentally determined that if a plant embryo is viewed through a sufficiently narrow slit (e.g., 30 μM), there is only a one-dimensional image produced because only a single row of CCD detector array elements will "see" the light, thereby producing a "line" image of the embryo. When this "line image" is split into component wavelengths in the vertical dimension, through the use of a prism-grating-prism monochromator 140, then the vertical dimension of the CCD detector array will consist of 320 lines, each displaying the slit-view at a different NIR wavelength. Or, conversely, each column will display the NIR spectrum of a single pixel-sized position along the longitudinal axis of the embryo. In this way, 256 spectra are obtained simultaneously in the brief time required to obtain a single image. Accordingly, in one aspect, the invention provides methods for non-invasively obtaining detailed measurements of gradients in near infrared (NIR)-revealed chemistry from a plurality of positions along the an axis of a living plant embryo and using the wavelength-by-position information to classify embryos.

As described in Example 1, it has been experimentally determined that in order to practice the methods of the invention, it is important to obtain smooth (non-noisy) spectra at extremely low light levels, which is not possible using a conventional imaging system, such as the system 100 shown in FIG. 1. The representative conventional imaging system 100 shown in FIG. 1 includes an imaging sensor with a two-dimensional array of individual detector elements (120), in line with a monochromator 140 (including a prism/grating/prism combination) having a slit aperture 142 (e.g., 30 μM wide for single pixel size capture), in line with an objective lens 150 aimed at a target 8 (e.g., a plant embryo).

Figure 2:
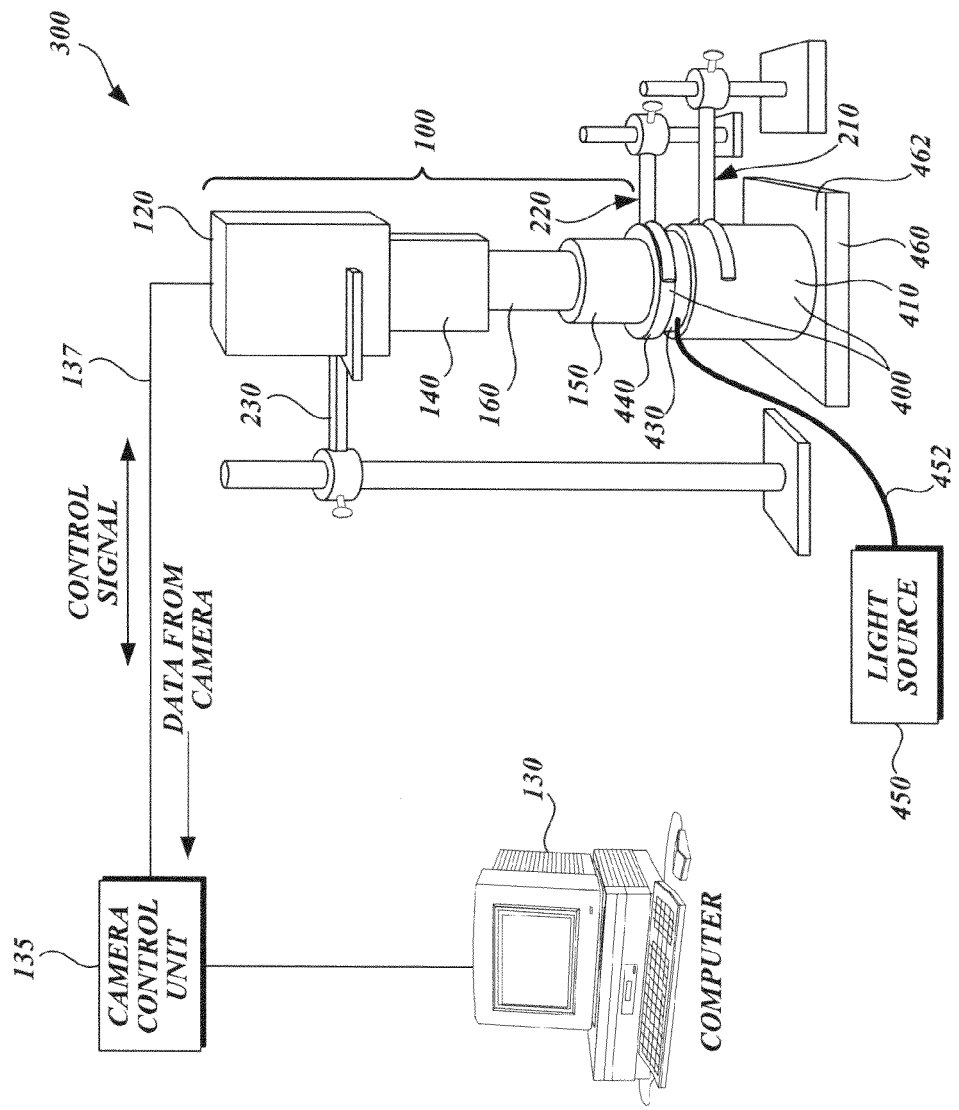
FIG. 2 is a schematic diagram showing a novel imaging system 300 for obtaining a hyperspectral line image including a light diffusing sample chamber 400, in accordance with an embodiment of the invention.
Figure 3:
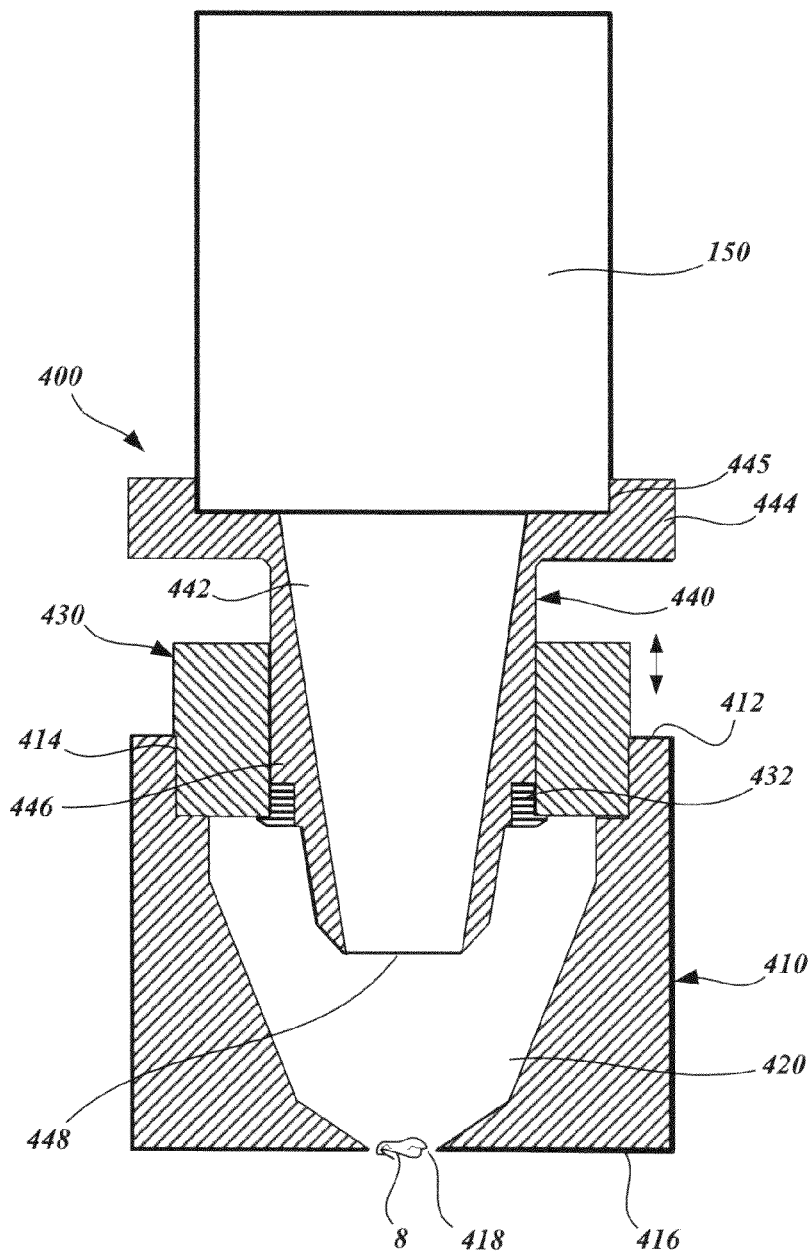
FIG. 3 illustrates a cross-sectional view of an embodiment of the light diffusing sample chamber 400 used for obtaining hyperspectral line images of embryos in accordance with an embodiment of the invention.

Therefore, the invention further provides a novel light diffusing sample chamber 400, as shown in FIGS. 2 and 3, for use with an imaging system 100, such as shown in FIG. 1, in order to obtain hyperspectral line images from a living specimen under low light and low heat conditions. In some embodiments, a novel imaging system 300 is provided, as shown in FIG. 2, which is a synergistic combination of an NIR-sensitive imaging sensor 120, a close-up objective lens 150, a monochromator (prism-grating-prism) 140, and a novel light diffusing sample chamber 400 with an optional integrated illumination means 430. The imaging system 300 may be used to non-destructively image a living specimen under low light and low heat conditions.

The novel methods and novel imaging system of the invention may be used to non-invasively obtain detailed measurements of gradients in near infrared (NIR)-revealed chemistry from a plurality of positions along an axis of a living specimen, such as a plant embryo or a plant seed. In some embodiments, the apparatus and methods may be used to obtain hyperspectral line images along an axis of a living specimen, such as a plant embryo or a plant seed.

Hyperspectral line (HLI) imaging refers to a plurality of spectral images containing spectroscopic information taken from different positions along a spatial line of a target, such as at least 5 spectral images, at least 10 spectral images, at least 50 spectral images, at least 100 spectral images, at least 250 spectral images up to 500 or more spectral images. All spectra across a spatial line in the image are recorded simultaneously.

Hyperspectral imaging (HSI) is a method of "imaging spectroscopy" that generates a two-dimensional image of a region of a target of interest having spectral data inherent in each pixel of the image based on local chemical composition of the target. Therefore, HSI combines the chemical specificity of spectroscopy with the spatial resolution of imaging. Light reflected from the target is separated into hundreds of wavelengths using a spectral separator and collected on a charge-coupled device (CCD) or a complementary metal oxide semiconductor (CMOS) sensor.

An exemplary camera for use in the methods and apparatus of the invention is a line imagine NIR spectral camera (commercially available from Specim, France), which acquires a line image at 256 contiguous spectral bands simultaneously in the 900-1700 nm range. The spectral camera preferably has high light throughput and can acquire more than 100 line images per second, with the acquisition of a sample at 320× 320 pixel resolution.

In some embodiments, the imaging system is configured to allow the capture of a complete NIR spectra for each pixel in a single line of pixels along an axis (e.g., the longitudinal axis) of a living plant embryo, which is output as wavelength-by-position data to at least one of a computer storage device, computer-readable media, or to a user interface.

In some embodiments, the spectral camera is mounted to a system to allow capture of multiple areas of the target, such as above a conveyer belt using the belt motion for scanning multiple positions on a target. For example, the use of a stepper motor and a moveable stage may be used with the imaging system 300 to acquire a series of line images in rapid succession. This would allow one to turn the line image into a whole embryo image.

The use of wavelength-by-position spectral information significantly increases the accuracy of classifying and selecting plant embryos, as described in more detail in Examples 4-6.

In accordance with the foregoing, in one aspect, the invention provides a light diffusing sample chamber for capturing a hyperspectral line image of a living specimen. The light diffusing sample chamber comprises (i) a first circular housing defining an interior cone-shaped reflecting chamber, the first housing having an opening on the top at the widest part of the reflecting chamber for receiving a second circular housing, and having an opening at the bottom of the chamber for receiving a specimen; and (ii) a second circular housing defining an interior cone-shaped chamber, the second housing having a top opening at the widest part of the chamber for connection to an imaging apparatus, and a bottom opening at the narrow part of the chamber, wherein the second housing is mounted above the first housing and a portion of the chamber protrudes into the reflecting chamber.

FIG. 3 provides a cross-sectional view of a representative embodiment of a light diffusing sample chamber 400. As shown in FIG. 3, the sample chamber 400 comprises a first circular housing 410 defining an interior cone-shaped reflecting chamber 420, and a second T-shaped circular housing 440 that functions as a lens shade, the second housing 440 defining an interior cone-shaped chamber 442. The first circular housing 410 has a top 412 with an circular opening 414 sized to receive a light ring 430 and a bottom 416 with an opening 418 sized to receive a specimen positioned on a specimen platform 460 (shown best in FIG. 2). As shown in FIG. 3, the opening 418 (specimen target area) in the bottom of the first housing 410 is located at the apex of the cone-shaped reflecting chamber 420. In operation, the reflecting chamber 420 concentrates diffuse light from the light ring 430 onto a specimen positioned in the opening 418, and the cone-shaped chamber 442 defined by the second housing (lens shade) 440 ensures that most of the light directed towards the lens 150 is light reflected from the specimen 8 positioned in the opening 418. In some embodiments, the cone-shaped reflecting chamber 420 has multiple angles designed to direct light from the illumination source 430 onto the specimen 8 in the opening 418, as shown in FIG. 3. The surface of the reflecting chamber 420 is preferably coated with a white reflective material, such as white titanium-oxide.

With continued reference to FIG. 3, the sample chamber 400 comprises the T-shaped second housing 440 (lens shade) with a top portion comprising a circular flange 444 with a circular opening 445 for removably receiving the objective lens 150, and a bottom circular shaft portion 446 that defines the interior cone-shaped chamber 442. The apex of the cone-shaped chamber 442 protrudes into the reflecting chamber 420. The interior surface of the chamber 442 is preferably black. The exterior of the bottom circular shaft portion 446 of the second housing 440 that protrudes into the reflecting chamber 420 is preferably white.

In operation of the system 300, the light diffusing sample chamber 400 is coupled to the imaging system 100 as follows. The objective lens 150 is positioned into the opening 445 of the circular flange 444 of the second housing 440. The objective lens 150 may be coupled to the second housing 440 with any suitable light-tight connection means, such as a screw connection, a snap-fit connection, a gasket, or the like. In a preferred embodiment, the objective lens 150 is connected to the second housing 440 with a spring-loaded connection, such that the objective lens 150 is released upon the downward movement of the second housing 440, as described in more detail below.

With continued reference to FIG. 3, the second housing 440 further comprises a bottom circular shaft portion 446 defining the lower portion of the cone-shaped chamber 442, having a circular opening 448 at the bottom of the chamber 442 centered over the target opening 418 of the first housing 410.

As shown in FIG. 3, the circular shaft portion 446 of the second housing 440 protrudes through the opening 414 on the top of the first housing 410, such that the cone-shaped chamber 442 and reflecting chamber 420 are stacked in a concentric manner, leaving a space between the circular shaft portion 446 and the edge defining the circular opening 414 on top of the first housing.

In some embodiments, the sample chamber 400 further comprises an illumination source, such as a fiber optic light ring 430 mounted around the shaft portion 446 of the second housing 440 and on top of the first housing 410 such that it spans the space between the circular shaft portion 446 and the edge defining the circular opening 414 on top of the first housing. Light is provided to the fiber optic light ring 430 from an illumination box 450 via a fiber optic cable 452 (shown best in FIG. 2). The light ring 430 may be mounted to the shaft portion 446 of the second housing using any suitable means, such as, for example, with a retaining ring 432.

In one exemplary embodiment of the sample chamber 400, the diameter of the exterior of the first housing 410 is 3.1 inches, the diameter of the opening 448 of the cone-shaped chamber defined by the second housing 440 is 0.65 inches, the distance from the bottom 416 of the first housing 410 and the bottom of the second housing 448 is 0.97 inches, and the total height of the second housing 440 is 2.4 inches.

As further shown in FIG. 2, in one embodiment of the system 300, a first support arm 210 having vertical movement is positioned around (e.g., via a bracket, clamp or the like) the first housing 410 of the light diffusing sample chamber 400. A second support arm 220 having vertical movement is positioned around (e.g., via a bracket, clamp or the like) the second housing 440 of the light diffusing sample chamber 400. A third fixed support arm 230 is positioned around (e.g., via a bracket, clamp or the like) the upper portion of the imaging system 100, such as the imaging sensor 120.

In one embodiment of the light diffusing sample chamber 400, the first circular housing 410 is slidably mounted to the second housing 440 and light ring 430 combination, such that the first housing 410 may be moved up and down in a vertical direction with respect to the specimen platform 460, via movement of the first support arm 210 to allow for loading of a specimen in the opening 418 for imaging. In one embodiment of the light diffusing sample chamber 400, the second housing 440 is supported by the second support arm 220 and also may be moved up and down in a vertical direction. The lens 150 attached to the imaging system 100 is in a fixed position supported by the third support arm 230. In a preferred embodiment, the first housing 410 is moved upward and the second housing 440 is moved downward, via the first 210 and second 220 support arms, respectively, thereby releasing the entire light diffusing sample chamber 400 from the objective lens 150.

In some embodiments of the system 300, positioned below the first housing 410 of the light diffusing sample chamber 400 is a movable specimen platform 460. The specimen (e.g., an embryo 8) is placed on the platform 460 and moved into the opening 418 of the bottom of the first housing 410. The top surface 462 of the platform 460 preferably comprises a Teflon (GORE-TEX®) material that is removably placed on the platform 460 prior to imaging. In one embodiment, the platform 460 is sized to receive a piece of 8×8 cm of Teflon material such as GORE-TEX®.

In operation of the system 300 comprising the light diffusing sample chamber 400, a specimen such as an embryo 8 is loaded into the opening 418 by raising the first housing 410 by sliding it vertically approximately 1 cm or more up with respect to the second housing 440. Two external cross-hair laser beams may be used to form two cross-hairs in the precise position viewed through the monochromator slit 142.

The user views the camera image on the target area through the monochromator slit. An embryo 8 is placed on the movable platform 460 and slid into position and rotated as necessary to align the horizontal cross-hair along the desired embryo axis. The first housing 410 is then lowered to the platform 460 containing the specimen 8 such that the bottom of the first housing 410 rests directly on the surface of the sample platform 460, thus excluding any stray light. Fine adjustments are then made by moving the platform slightly while viewing the image on the screen until the length and sharpness of the spectral image is maximized. The fiber optic light ring 430 shines light into the reflecting chamber 420 (with white interior surface) to illuminate the specimen 8 positioned in the opening 418. The flange 444 of the second housing (lens shade) forms a light tight connection around the objective lens 150, and the cone-shaped chamber 442 (with black interior surface) excludes stray reflected light and only captures the light reflected off the target embryo specimen positioned in the opening 418. Multiple spectral line images are then captured of the specimen, typically at least 5 to 100 images, which are then typically averaged to form a single spectral image. In a preferred embodiment, at least 5 (e.g., at least 10, at least 20, at least 50, at least 60, at least 100 up to 500 or more) images are captured per specimen and averaged together. In a preferred embodiment of the system 300, the imaging apparatus is capable of capturing each image within 100 milliseconds, such that capture of 64 images takes only 6.4 seconds. Exemplary methods of spectral image data capture and analysis are provided in Examples 1-6 herein.

In another aspect, the invention provides an imaging system for capturing reflectance spectral images from a living sample. The imaging system comprises an image sensor, a monochromator, an objective lens, and a light diffusing sample chamber for capturing a hyperspectral line image of a living specimen, the light diffusing sample chamber comprising (i) a first circular housing defining an interior cone-shaped reflecting chamber, the first housing having an opening on the top at the widest part of the reflecting chamber for receiving a second circular housing, and having an opening at the bottom of the chamber for receiving a specimen; and (ii) a second circular housing defining an interior cone-shaped chamber, the second housing having a top opening at the widest part of the chamber for connection to an imaging apparatus, and a bottom opening at the narrow part of the chamber, wherein the second housing is mounted above the first housing and a portion of the chamber protrudes into the reflecting chamber.

FIG. 2 is a schematic diagram showing a representative embodiment of an imaging system 300 comprising the light diffusing sample chamber 400 for obtaining a hyperspectral line image in accordance with an embodiment of the invention. As shown in FIG. 2, the imaging system 300 comprises an image sensor 120 for capturing wavelength-by-position spectral data, a monochromator 140 having a slit 142, an objective lens 150, and a light diffusing sample chamber 400. The sample chamber 400 comprises (i) a first circular housing defining an interior cone-shaped reflecting chamber, the first housing having an opening on the top for receiving a second circular housing, and having an opening at the bottom for receiving a sample; and (ii) a second circular housing defining a cone-shaped chamber, the second housing having a top opening for receiving the objective lens in a light-tight connection, and a bottom opening, wherein the cone-shaped chamber is mounted above and protrudes into the reflecting chamber and is centered over the sample receiving opening.

In operation, the system 300 rapidly (such as, for example, in 6 seconds or fewer) provides 256 spectra along a desired axis (e.g., the length of an embryo), thereby allowing for rapid data capture and analysis of a plurality of embryos, while maintaining the viability of the sample without the need for long exposure to an illumination source. As shown in FIG. 2, the system 300 includes the light diffusing sample chamber 400 with an integrated illumination source 430, as described supra. As described in Examples 1 and 2, it has been experimentally determined that the light diffusing sample chamber 400 provides the system 300 with the ability to obtain smooth (non-noisy) spectra at extremely low light levels. The NIR wavelength-by-position data generated using the system 300 allows for selection and/or the ability to distinguish groups of embryos from one another, as described in more detail herein.

Although the sample chamber 400 and imaging system 300 have been discussed primarily in the context of a system for imaging living biological specimens, the present invention is suitable for other imaging applications and may be tailored correspondingly.

In one aspect of the invention, a method is provided for classifying plant embryos. The method comprises (a) developing a classification model by (i) acquiring reflectance spectral raw data from a plurality of positions along a desired axis of a plurality of embryo samples of a known embryo type; (ii) performing a data analysis by applying one or more classification algorithms to the spectral raw data, the data analysis resulting in development of a classification model for classifying plant embryos by embryo type; (b) acquiring reflectance spectral raw data from a plurality of positions along the corresponding axis of a plant embryo of unknown embryo type; and (c) applying the developed classification model to the spectral raw data of step (b) in order to classify the type of plant embryo of unknown embryo type.

Figure 4A:
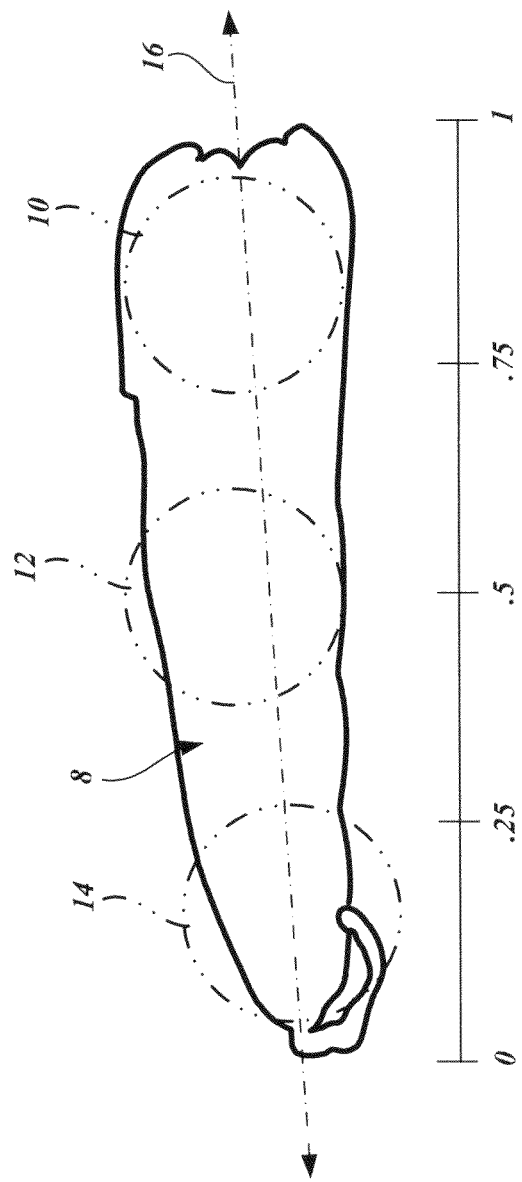
FIG. 4A illustrates a diagrammatic representation of a tree embryo 8. The circled areas represent the embryo regions representative of the three embryo organs known as cotyledon 10, hypocotyl 12, and radicle 14, the embryo having a longitudinal axis 16.

Embryos from all plant species can be adapted to the inventive methods. The methods have particular application to agricultural plant species where large numbers of somatic embryos are used to propagate desirable genotypes such as with forest tree species. In particular, the methods can be used to classify somatic embryos from conifer tree family Pinaceae, particularly from the genera *Pseudotsuga* and *Pinus*. A diagrammatic drawing of a *Pseudotsuga* tree embryo 8 is presented in FIG. 4A in which the general locations of the three embryo organs (cotyledon 10, hypocotyl 12, and radicle 14) and longitudinal axis 16 are indicated.

The method first develops a classification model by acquiring complete reflectance spectra for each pixel in a single line of pixels along an axis of an embryo of a known embryo type and processing the data using classification algorithms. The method may be practiced by acquiring reflectance spectra from any axis of the embryo, such the longitudinal axis 16, or a diametric axis at a selected position on the embryo (e.g., the cotyledon 10, hypocotyl 12 or radicle 14).

In one embodiment, prior to making the classification model, the spectral data is split into component wavelengths from 900 to 1680 nm, detected by a 2-D image sensor, and the data is output in wavelength-by-position format to at least one of a computer storage device, computer-readable media or to a user via a user interface (e.g., a computer screen). The spectral data may also be preprocessed to reduce noise and adjust for drift and diffuse light scatter. The classification model is then made by performing a data analysis using classification algorithms on the spectral data.

Reflectance spectral data is then obtained from a corresponding axis for a plant embryo of an unknown type. The spectral raw data collected from the embryo of unknown type is either applied directly to the embryo quality classification model or preprocessed to reduce noise and adjust for drift and diffuse light scatter, and then the preprocessed spectral data is applied to the classification model depending upon which method was used to make the classification model in use. In either case, the application of the unknown spectral data to the classification model allows classification of the type to the plant embryo of unknown plant embryo type.

In some embodiments of the methods, the spectral data is obtained from plant embryos using the imaging system 300 described herein. A classification model for plant embryo quality is then developed by performing a data analysis on the wavelength-by-position data using one or more classification algorithms. Examples of such classification algorithms include, but are not limited to, principal components analysis [see, for example, Jackson, J. E., *A User's Guide to Principal Components*, John Wiley and Sons, New York (1991); Jolliffe, I. T., *Principal Components Analysis*, Springer-Verlag, New York (1986); Wold, S., "Pattern recognition by means of disjoint principal components models," *Pattern Recognition* 8:127-139 (1976); and Watanapongse, P., and H. H. Szu, "Application of Principal Wavelet Component in Pattern Classification," Proceedings of SPIE, *Wavelet Applications V*, H. H. Szu, Editor, Vol. 3391, pp. 194-205 (1998)), artificial neural networks (Mitchell, Tom M., *Machine Learning*, WCB/McGraw-Hill pp. 112-115, (1997)], Bayesian Classifiers (Mitchell at 174-176), Probably Approximately Correct (PAC) Learning (Mitchell at 203-220), Radial Basis Functions which includes the statistical technique of fitting mixture distribution models to data (Mitchell, pp. 238-240), and Nearest-Neighbor Methods (Mitchell at 231-236). In addition to the aforementioned classification algorithms, a classification algorithm is provided in the present invention to classify plant embryos based upon the Lorenz curve. For a brief introduction to Lorenz curves, see Johnson, S., and N. L. Kotz, Eds., *Encyclopedia of Statistical Sciences*, John Wiley, Vol. 5, pp. 156-161 (1985).

It is also well known in the art of data analysis that several different algorithms besides Principal Component Analysis (PCA) can be used to develop and use classification models.

More specifically, the following statistical techniques can also be adapted to the present invention: Partial Least Squares Regression, Principal Components Regression (PCR), Multiple Linear Regression Analysis (MLR), Discriminant Analysis, Canonical Correlation Analysis, Multivariate Multiple Regression, Classification Analysis, Regression Tree Analysis, which includes Classification Analysis by Regression Trees (CART™, Salford Systems, San Diego, Calif.), and Logistic and Probit Regression. See U.S. Pat. No. 5,842,150 and Mitchell, Tom M., Machine Learning, WCB/McGraw-Hill, pp. 112-115, 238-240 (1997).

The classification model is deduced from a "training" data set of multiple spectral data sets of plant embryos acquired from embryos of a known type (i.e., having known embryo qualities or known morphological features). Embryos providing the training set data are classified into types based on biological fact data such as, for example, morphological similarity to normal zygotic embryos or proven ability to germinate or convert to plants. The inventive methods are generally adaptable to any plant feature that is measurable and susceptible to quantification. Unclassified embryos are classified according to type based upon how close the spectral data of the unclassified embryos fit to the classification model developed from the training set groups.

As used herein, the term "classification algorithm" refers to any sequence of mathematical or statistical calculations, formulae, functions, models, or transforms of image or spectral data from embryos used for the purpose of classifying embryos according to embryo type. A classification algorithm can have just one step or many. In addition, classification algorithms of the present invention can be constructed by combining intermediate classification models or single metric classification models through the use of mathematical algorithms such as the Bayes optimal classifier, neural networks, or the Lorenz curve. Except for the single metric classification models, the image classification models of the present invention are derived from a spectral data analysis of a plurality of positions along an axis of the embryo, such as at least 5 positions, at least 10 positions, at least 20 positions, at least 50 positions, at least 75 positions, or at least 100 positions. In one embodiment, the spectral data analysis is from at least 100 positions along the longitudinal axis of a plant embryo.

Thus, the classification algorithms perform a data analyses that results in the development of a classification model from the spectral data without any subjective assumptions being made regarding which data features are important for embryo type classification.

Optionally, the raw digital image data can be preprocessed using preprocessing algorithms. As used hereafter, the term "preprocessing algorithm" refers to any sequence of mathematical or statistical calculations, formulae, functions, models, or transforms of image or spectral data from embryos used for the purpose of manipulating spectral data in order to: (1) remove spectral data that is derived from non-embryo sources, i.e., background light scatter or other noise sources; (2) reduce the size of the digital data file that is used to represent the acquired spectra of the embryo while retaining substantially all of the data that represents informational features such as geometric embryo shape and surface texture, color, and light absorption, transmittance, or reflectance, of the acquired spectra; and (3) calculate metrics from the acquired spectral data and from values obtained during other preprocessing steps in order to identify and emphasize embryo data that is useful in development of an embryo quality classification model.

For example, U.S. Pat. No. 5,842,150 discloses that NIR spectral data can be preprocessed prior to multivariate analysis using the Kubelka-Munk transformation, the Multiplicative Scatter Correction (MSC), e.g., up to the fourth order derivatives, the Fourier transformation, or by using the Standard Normal Variate transformation, all of which can be used to reduce noise and adjust for drift and diffuse light scatter.

Alternatively, the amount of digital data required to represent an acquired spectrum of an embryo can be reduced using preprocessing algorithms such as wavelet decomposition. See, for example, Chui, C. K., *An Introduction to Wavelets*, Academic Press, San Diego (1992); Kaiser, Gerald, *A Friendly Guide to Wavelets*, Birkhauser, Boston; and Strang, G., and T. Nguyen, *Wavelets and Filter Banks*, Wellesley-Cambridge Press, Wellesley, Mass. Wavelet decomposition has been used extensively for reducing the amount of data in an image and for extracting and describing features from biological data. For example, wavelet techniques have been used to reduce the size of fingerprint image files to minimize computer storage requirements. A biological example is the development of a method for diagnosing obstructive sleep apnea from the wavelet decomposition of heart beat data. Wavelets enable rearrangement of the information in a picture of an embryo into size and feature categories. For example, size and shape data may be separated from texture. The results of a wavelet decomposition or functions thereof are then used as inputs to the classification algorithms described above. A variety of other interpolation methods can be used to similarly reduce the amount of data in an image or spectral data file, such as calculation of adjacent averages, Spline methods (see, for example, C. de Boor, *A Practical Guide to Splines*, Springer-Verlag, 1978), Kriging methods (see, for example, Noel A. C. Cressie, *Statistics for Spatial Data*, John Wiley, 1993), and other interpolation methods which are commonly available in software packages that handle images and matrices.

Other preprocessing algorithms can be used to process data collected from an embryo in order to obtain the most robust correlation of the acquired data to embryo type. For example, as described in co-pending U.S. patent application Ser. No. 11/836,095, incorporated herein by reference, and as described in Example 3, several statistical values were calculated from data obtained from single patch imaging analysis of whole embryos to recapture some of the data information that was lost when a wavelet decomposition was used to reduce the size of the image. The recaptured information represented in the metrics allowed the development of a classification model that was better at predicting embryo type than a model developed from principal component analysis of image data that was preprocessed using wavelet methods. Such preprocessing algorithms may be applied to the wavelength-by-position data obtained as described herein to provide classification models of increased accuracy as compared to such models based on data obtained from single-patch analysis.

As used hereinafter, "metrics" refers to any scalar statistical value that captures geometric, color, or spectral features that contain information about the embryos, such as central and non-central moments, function of the spectral energy at specific wavelengths, or any function of one or more of these statistics. In image processing language, sets of metrics are also known as feature vectors. In addition, metrics can be derived from external considerations, such as embryo processing costs, embryo processing time, and the complexity of an assembly line sorting embryos by quality.

In another embodiment of the present invention, desired axis regions of a plurality of embryos are scanned and spectral data is acquired regarding NIR reflectance of electromagnetic radiation (hereinafter referred to as light) at multiple wavelengths ranging from 900 nm to 1680 nm. Differences in spectral data collected from various types of embryos (for example, high conversion potential or high morphological similarity to normal zygotic embryos, or somatic embryos of a particular genotype) are presumed to reflect differences in chemical composition that are related to embryo type. For example, embryo type may be designated as embryos with high quality. Numerous studies assert that embryo quality is related to gross chemical composition of the embryo or its parts, especially the amounts of water and storage compounds (proteins, lipids, and carbohydrates). Some examples include: Chanprame, S., T. M. Kuo, and J. M. Widholm, "Soluble carbohydrate content of soybean [*Gycine max* (L.) Merr.] somatic and zygotic embryos during development," *In Vitro Cell Dev. Biol-Plant.* 34:64-68 (1998); Dodeman, V. L., M. Le Guilloux, G. Ducreux, and D. de Vienne, "Somatic and zygotic embryos of *Daucus carota* L. display different protein patterns until conversion to plants," *Plant Cell Physiol.* 39:1104-1110 (1998); Morcillo, F., F. Aberlenc-Bertossi, S. Harnon, and Y. Duval, "Accumulation of storage protein and 7S globulins during zygotic and somatic embryo development in *Elaeis guineensis,*" *Plant Physiol. Biochem.* 36:509-514 (1998); and Obendorf, R. L., A. M. Dickerman, T. M. Pflum, M. A. Kacalanos, and M. E. Smith, "Drying rate alters soluble carbohydrates, desiccation tolerance, and subsequent seedling growth of soybean (*Glycine mac* L. Merrill) zygotic embryos during in vitro maturation," *Plant Sci.* 132:1-12 (1998).

Spectrometric analysis of embryos can be performed using a conventional data collection setup that includes a light source, a microscope, a light sensor, and a data processor. Preferably, each embryo region undergoes multiple light scans in order to obtain a representative average spectrum. In addition, it is useful that the data processor include a built-in calibration program which is run periodically throughout the data collection phase to recalibrate the internal baseline to correct for dark current, and to recalibrate against the standard white background material upon which the embryo sits. In some embodiments, the spectrometric analysis of embryos is performed using the imaging system 300, described herein including the sample chamber 400, to allow for imaging under low light conditions.

In one embodiment, the method of classifying embryos according to type (as defined above) by the NIR spectrometric measurements (wavelength-by-position) comprises two main steps. The first step is the development of a classification model, involving the substeps of development of training and cross validating sets. Spectral data is acquired from a plurality of positions along a desired axis (e.g., the longitudinal axis) of embryos of a known embryo type, optionally a preprocessing of the acquired spectral data is performed, and then a data analysis is performed using one or more classification algorithms to develop a classification model for embryo type. The second main step is the acquisition of spectrometric data from the corresponding axis (e.g., the longitudinal axis) of an embryo whose type is unknown, optionally performing preprocessing of the acquired spectral data, followed by data analysis of the acquired spectral data using the classification model developed in the first main step.

Model training sets consist of a large number of reflectance spectra acquired from embryos that have a known type. The training sets are used in the classification algorithms to develop a classification model. As previously noted, a variety of preprocessing algorithms are available that can be used to first reduce noise and adjust for base line drift. However, for some data sets, it may not be necessary to preprocess the data to reduce background noise.

There are many data analysis methods that can be applied to develop and use classification models that allow plant embryos to be classified by type. The above-described mathematical methods are a sampling of some of the major techniques. However, it should be emphasized that data analysis techniques can be put together in an almost infinite number of combinations to achieve the desired results. For example, a soft independent modeling of class analogy (SIMCA) method can be used on images of embryos which have their position by wavelength information collapsed into a single array using principal components and then the result can be shrunk using wavelets. SIMCA can then be used to build principal component regression models for each classification category. The Bayes optimal classifier can then be used to combine the classification decisions from six SIMCA model pairs. Partial least squares regression can be used in place of principal component regression in the SIMCA step. Similarly, neural networks can be used in place of Bayes optimal classifier to combine classification decisions into a final classification model.

In addition, the methods described for classifying plant embryos using embryo image NIR reflectance spectral data can be combined together in a number of different ways. For example, data analysis of the acquired raw visual and spectral data can be performed in parallel to develop a unitary classification model, or the analysis can be conducted in series whereby two independent classification models are developed using the image and spectral data separately. Many permutations of the methods described herein are possible to accomplish the classification of plant embryos by embryo quality.

In another aspect, the invention provides a method for classifying a plant embryo of an unknown type based on near infrared spectroscopy imaging. The method according to this aspect of the invention comprises (a) illuminating an axis of a plant embryo of unknown type; (b) capturing a hyperspectral line image from the light reflected off the illuminated plant embryo; (c) splitting the infrared portion of the captured line image into component wavelengths from 900 to 1680 nm; (d) detecting the split line image with a detector array; (e) outputting the detected image as wavelength-by-position data to at least one of a computer storage device, computer-readable media, or a user interface; and (f) comparing the wavelength-by-position data obtained from the axis of the embryo of unknown type to wavelength-by-position data of a reference plant embryo of known type to classify the plant embryo.

Examples 1-6 illustrate the inventive methods, imaging apparatus and systems and the use of them to classify different types of plant embryos, including somatic embryos of different genotypes, zygotic embryos, and embryos that are most likely to be successfully germinated and produce normal plants. The apparatus, system, and methods described herein and further illustrated in Examples 1-6 can be readily adapted to continuous examination of somatic embryos as might be required in a large scale production facility. For example, these systems and methods can be used together to create an efficient and cost-effective screening methodology for classifying somatic embryos by their germination potential.

EXAMPLE 1

This Example describes an experiment using a conventional imaging system to determine if hyperspectral line image data could be generated that would be suitable for use in classifying embryos according to type.

Methods:

NIR spectra were collected simultaneously from 250 positions along a single-pixel line running from top to bottom from a plurality of plant embryos (i.e., along the longitudinal axis of the embryo).

Equipment Set Up:

A conventional imaging system was tested to determine if hyperspectral line images could be obtained from plant embryos. As shown in FIG. 1, the conventional imaging system 100 included an Indigo α-NIR camera 120 (from FLIR Systems, Inc.) linked to a computer 130 (not shown) containing software for controlling the camera 120 with 2-D image sensor (spatial axis 121, spectral axis 122) (commercially available from IRVista with software from FLIR Systems, Inc.) affixed on top of a monochromator 140 including a prism 144/grating 146/prism 148 "PGP" combination (Specimen diffraction grating from Spectral Imaging Ltd), which was mounted on top of an objective close-up lens 150/extension tube 160 combination for magnification (from Navitar 75 mm F1.3 TV lens with 12 cm of C-mount extension tubes).

As shown in FIG. 1, in operation of the imaging system 100, the magnified image of light reflected from an embryo 8 target (positioned on a piece of Gore-Tex®) passes through the objective lens 150 then through a 30 µM slit aperture 142 into the monochromator 140. The slit 142 blocks all but a single line of the image of the embryo target. The lenses and the PGP combination within the monochromator 140 then splits the infrared portion of the incoming line image into component wavelengths from 900 to 1680 nm, and focuses these onto the camera's 120 detector array in a direction perpendicular to the embryo's longitudinal axis (e.g., vertically).

Results:

As described above, the imaging system 100 was used to attempt to obtain a hyperspectral line image from a target line of 5 mm long (i.e., the longitudinal axis of an embryo). The image formed on the 320×256 detector array consisted of 256 horizontal lines and 320 vertical lines. Each horizontal line would represent the view of the embryo's longitudinal axis seen through the slit 142 at a different NIR wavelength (spectral axis). Each vertical line would represent the NIR spectrum at successive single-pixel points along the length of the embryo (spatial axis).

After analyzing the images of the embryos obtained using the system 100, it was determined that the conventional imaging system 100 did not provide hyperspectral line image data suitable for embryo classification. Rather, the low light signal from the conventional imaging system 100 resulted in unacceptably noisy spectra. In particular, it was determined that the pixel luminance frequency histogram of the reference background (Gore-Tex®) had a peak value of less than 500 units on a scale of 0 to 4096 grayscale units.

The light signal was very low because each pixel in the vertical direction of the image only captures a narrow waveband of about 3 nm=[(1680−900)/256]. Because the slit 142 only allowed about 3% of the embryo's reflected light to pass into the monochromator 140, only 1/125th (0.4%) of this light was split to each detector in the camera's array 120. Therefore, the amount of NIR light reaching each detector element in the camera's array 120 was only about 0.012% of that normally obtained using a circular field of view (e.g., 0.7 mm diameter), otherwise referred to as "a patch" of whole-embryo spectroscopy.

In addition to the problem of noisy spectra due to the low light, it was also determined that the images produced by the conventional system 100 were also dominated by shadows due to positioning of two halogen source lamps, small variations in Gore-Tex® background signal and other sources of stray light that could enter the slit 142. In this regard, it was observed that even the operator's body position caused noticeable changes. Therefore, it was concluded that the spectral data obtained from the conventional system 100 was not suitable for embryo classification.

EXAMPLE 2

This Example describes the use of a novel light diffusing sample chamber 400 in an imaging system to obtain a hyperspectral line image from a target line of 5 mm (i.e., the longitudinal axis of a plant embryo) under low light that are suitable for use in plant embryo classification methods.

Methods:

The conventional system 100 described in EXAMPLE 1 was modified to include a light diffusing sample chamber 400 removably mounted to the lens 150/extension tube 160 combination, as shown in FIG. 2. In particular, the objective lens 150 in the imaging system 100 was removably attached to the upper circular flange portion 444 of the second housing 440 (lens shade) to provide the imaging system 300, as shown in FIG. 2.

FIG. 3 shows a detailed cross-sectional view of a representative embodiment of the light diffusing sample chamber 400 attached to the objective lens 150. As shown in FIG. 3, the light diffusing sample chamber 400 comprises three main components: (1) a first housing 410 defining an interior cone-shaped reflecting chamber 420 having a bottom opening 418 near the apex of the cone-shaped reflecting chamber for placement of a sample; (2) a second housing 440 (lens shade) comprising a top circular flange portion 444 for coupling the chamber 400 to an objective lens 150, and a bottom shaft portion 446 defining the bottom of a cone-shaped chamber 442; and (3) an integrated light ring 430. The chamber 442 defined by the second housing 440 (lens shade) is mounted over and partially protrudes into the reflecting chamber 420, with both chambers centered over the target area 418. The interior surface of the cone-shaped chamber defined by the second housing 440 (lens shade) is preferably black. The interior surface of the cone-shaped reflecting chamber 420 is preferably white.

A light ring 430 is mounted around the junction of the first housing 410 and the second housing 440 such that light shines down into the reflecting chamber 420 and illuminates the target area 418. Light is provided to the ring 430 by connecting the other end of the fiber optic cable 452 to a Bausch & Lomb illumination box 450 containing a 150 watt quartz-halogen-tungsten lamp.

The first housing 410 is slideably connected to the second housing 440 to allow vertical motion of the first housing 410 with respect to the second housing 440 to allow for placement of a biological specimen such as an embryo into the target area 418 for imaging.

In some embodiments, the system 300 further includes a specimen platform 460. The specimen platform 460 is preferably a moveable platform positioned below the target area 418 of the reflecting chamber 420. The surface 462 of the specimen platform 460 preferably comprises a piece (e.g., 8×8 cm) of Teflon (Gore-Tex®) that is replaceably fastened to the platform. To load a specimen such as an embryo into the target area 418 of the light diffusing sample chamber 400, the first housing 410 is raised by sliding it approximately 1 cm or more up in relation to the second housing 440, while the second housing 440 is moved downward a small distance, which frees the entire sample chamber 400 to be removed from the objective lens 150 and swung to the side.

In the system 300, two external cross-hair line lasers may then be used to position the embryo in line with the monochromator slit 142. For initial alignment purposes, first a printed black and white 5 mm×1 mm target is placed in the target area 418, viewed on the computer screen and centered in the target area 418 to the precise position viewed through the monochromator slit 142. The two external cross-hair line laser beams are then adjusted to form two cross-hairs on this position. This initial alignment needs to be done only once and then checked occasionally or when it is suspected that the lasers may have been accidentally knocked out of alignment.

An embryo is then placed on the movable platform 460 and slid into position in the cross-hairs and rotated as necessary to align the horizontal cross-hair along the desired axis (e.g., the embryo's longitudinal axis).

Once the system 300 is aligned with an embryo placed in the target area as described above, the entire sample chamber 400 is moved laterally back into position; the first (lower) housing 410 is lowered over the sample, so that it rests directly on the platform 460 containing the embryo such that the bottom 416 of the first housing 410 rests directly on the surface of the sample platform 460, thus excluding any stray light. The second (upper) housing 440 is raised to again form a light-tight seal against the objective lens 150. A user then views the camera image displayed on the computer screen 130 of the target area 418 through the monochromator slit 142. Fine adjustments are then made by moving the platform 460 slightly (either through manual or computer aided controls) while viewing the image on the computer screen 130 until the length and sharpness of the spectral image are maximized.

Results:

With the use of the imaging system 300, it was determined that uniform (virtually shadow-free) lighting was provided through the fiber optic light ring 430 (e.g., Edmond Optics No. 55707) placed above the reflecting chamber 420 at a distance of about 5 cm above the biological specimen (5 mm long, placed in the target area 418). It was also determined that diffuse light from the light ring 430 was further concentrated on the target area 418 by the interior multi-angled reflecting chamber 420 with a white titanium-oxide-coated interior surface. The second housing 440 functioned as a lens shade to exclude light from entering the lens that was not reflected off the embryo.

It was determined that the imaging system 300 with light diffusing sample chamber 400 resulted in a pixel luminance frequency histogram of the reference background (Gore-Tex®) with a peak at approximately 1000 on a scale of 0 to 4096 grayscale units, which was much improved over the <500 unit peak value and high spatial variation originally obtained using the imaging system 100 described in EXAMPLE 1. The imaging system 300 was capable of rapid image capture. For example, once the specimen was placed in position, the imaging process was begun in "video" mode to obtain 64 images of the specimen for averaging, which took a total of 6.4 seconds.

EXAMPLE 3

This Example describes mathematical methods that may be used to classify embryos based on NIR wavelength-by-position data obtained using the imaging system 300 of the invention.

Methods:

The following mathematical methods were used to calculate statistical values from data obtained from single patch imaging analysis of whole embryos as described in co-pending U.S. patent application Ser. No. 11/836,095, incorporated herein by reference.

The methods described in this Example may also be applied to the NIR wavelength-by-position data obtained using the imaging system 300 of the invention in order to develop a classification model for classifying plant embryos by embryo type. There are three main steps in using NIR wavelength-by-position data to separate embryos into different types. They are (1) obtaining smooth (non-noisy) NIR spectra at low light levels from a desired axis (e.g., longitudinal axis) of embryos of known types; (2) standardizing the spectral data with respect to a background control and adjustment for dark current; and (3) applying one or more classification algorithms to develop and use a classification model for plant embryo type.

Embryo Classification Models

Principal Component Analysis/Simca

The primary classification method used in the Examples of the present invention was soft independent modeling of class analogy SIMCA. See Jolliffe, I. T., *Principal Component Analysis*, Springer-Verlag, p. 161 (1986). SIMCA was used on each set of reduced images and metrics. This resulted in six intermediate classifications of each embryo. These six intermediate classifications were combined using the Bayes optimal classifier. See Mitchell, Tom M., *Machine Learning*, WCB/McGraw-Hill, pp. 174-176, 197, 222 (1997). SIMCA works by calculating a separate set of principal components for each category based on training data. The principal components which account for the majority of the variation are kept. Then, data from a new sample is regressed on the principal components from each group. The residual mean square errors are calculated for each category. The category with the smallest residual mean square error is the category to which the new sample is assigned. Six SIMCAs are done for each embryo.

Combining the Intermediate Claissifications Using the Basis Optimal Classifier

Two to six or so intermediate classifications can be combined into a single classification rule by first converting the resulting strings of zeros and ones into a binary code. For two intermediate classifications, there are four binary binations; for three intermediate classifications, there are eight binary combinations, and so on. For 'k' intermediate classifications, there are $2^k$ binary combinations. Each binary combination is assigned a label or code. For each embryo quality class, the probability of observing each code is estimated. Then the embryo-quality-class-by-binary-code probabilities are divided by the probability of the corresponding code occurring in all the data from both embryo quality classes. The resulting probabilities are the conditional probability of an embryo quality class given a code. An embryo's binary code is calculated and the embryo is assigned to the embryo quality class for which the conditional probability is highest for the observed binary code. Ties can be assigned randomly or assigned to one of the embryo quality classes based on other considerations such as economics.

Using the Lorenz Curve for Classifying Embryos

Originally, the Lorenz curve was developed to compare income distribution among different groups of people. A Lorenz curve is created by plotting the fraction of income versus the fraction of the population that owns that fraction of the income. In the present invention, the Lorenz curve is viewed as a comparison of two paired cumulative distribution functions where the fractional values of one cumulative distribution function are plotted verses the fractional values of the second cumulative distribution function. If the two distributions are the same, the Lorenz curve will plot the straight line y=x. The point farthest from the line y=k corresponds to the balance point between accumulating more of one distribution than the other. The balance or extreme point is an objective point at which to separate the two distributions.

The Lorenz curve classification method of the present invention has four steps. First, Lorenz curves are calculated for each metric in a set of metrics. The points on these Lorenz curves the furthest from the line, y=x, are found. Second, the metric values corresponding to the extreme points on the Lorenz curves are used as the threshold values to make single metric classifications of the embryos: values of a metric less than its threshold are assigned to one embryo quality class and values greater than the threshold are assigned to the other embryo quality class. Third, the set of metrics is subsetted to reduce the number of combinations that must be searched in the final stage. Fourth, pairs, triples, quadruples, etc., of the single metric classifications are combined into binary codes and used in the Bayes optimal classifier to create classification models for assigning embryos to one of two quality classes. Classification models are made for all possible pairs, triples, quadruples, etc., and the best model is retained in each case.

Calculating the Lorenz Curve for a Single Metric

The metric values for the two embryo quality classifications are combined and all the distinct metric values identified. Alternatively, the minimum and maximum value of all the metric values for both embryo quality classifications combined are found and a user-specified number of equally spaced steps between the minimum and maximum are used. When there are too many distinct values, this second option is useful. In either case, for each distinct metric value, the fraction of metric values less than or equal to the distinct value is recorded for each embryo quality class. Thus, two paired cumulative distribution curves are obtained. Plotting these two sets of fractions against each other constitutes the Lorenz curve. If the two distributions are the same, the Lorenz curve is the line, y=x.

Finding the Extreme Points on the Lorenz Curves

The distance of a point, $(x_0, y_0)$ from the line, y=x, is the absolute value of the difference between $y_0$ and $x_0$ divided by the square-root of two: $|y_0-x_0|/\sqrt{2}$. The absolute value of the difference between the cumulative distribution functions of the two classes of embryo quality for a metric is searched for its highest point. The corresponding metric value is used as the threshold. This extreme point is the balance point between one distribution accumulating more probability than the other distribution. The extreme point was used as the threshold in the metric classification models developed in Example 4. Other points on the Lorenz curve may be used as thresholds based on other considerations, such as processing costs. If a point other than the extreme point is used as the threshold, the Lorenz curve can be used to determine the tradeoff in misclassification error rates.

Single Metric Classifications

Metric values less than the threshold are assigned to one of the embryo quality classes and values greater than the threshold are assigned to the other quality class. These single metric classifications result in an embryo metric value being assigned a zero or one. This is done for each metric used: one embryo quality class is set to one and the other is set to zero. Several single metric classifications can then be combined to yield a final classification that has a lower misclassification error rate than any of the individual single metric classifications.

Combining the Lorenz Curve Single Metric Classifications Using the Bayes Optimal Classifier Two or more single metric classification models can be combined into a single classification rule using the same Bayes optimal classifier method previously described to combine intermediate SIMCA classification models. Alternatively, single metric classification models or intermediate SIMCA classification models can serve as the input data to neural network algorithm to arrive at a final classification model for plant embryo quality. However, as described below, when single metric classification models are combined to arrive at a final classification rule special problems arise.

Substituting the Metrics to be Combined into a Single Classifications Model

The Lorenz curve can be used to find an optimal threshold value for a single metric. Optimal is here defined in the sense of balancing probability accumulation. However, the Lorenz curve cannot handle the case when several metrics are considered together because the Lorenz curve can only compare two distributions at a time. One solution is to feed sets of metrics into an artificial neural network to find an optimal classification rule. However, with hundreds of metrics, it would be necessary to either fit very large networks or fit a very large number of small networks. For the purpose of this application, the simpler the classification rule, the better. It is recognized that the thresholds found for individual metrics may not be the best ones to use when combining several metrics through their single metric classifications. Nevertheless, it is possible to search large numbers of combinations of single metric classifications by calculating the results of the Bayes optimal classifier approach outlined above and comparing them for various combinations of the single metric classifications. Yet there are still limitations on the number of combinations that can be searched. When there are 682 metrics being considered, there are 8.935 billion distinct four-metric combinations alone. As computers get faster, such a number will not pose much of a problem. However, for limited computing hardware, subsetting the metrics will greatly reduce the amount of work.

Two subsetting criterion present themselves. First, the metrics whose single metric classifications are above some limit can be kept. Second, many of the metrics are correlated with each other. The metrics highly correlated with the better metrics can be dropped from consideration since they are informational twins to the better metrics: a metric perfectly correlated with another contains no information not already in the other metric. Metrics with very low correlations among them are more likely to create useful binary codes. These subsetting criterion can be used together to reduce the number of metrics.

Several different examples of classification techniques using hyperspectral line data from embryos are specifically demonstrated in the Examples 4-6.

EXAMPLE 4

This Example describes the collection of hyperspectral line data from Loblolly pine embryos from six different embryo groups using the imaging system 300 comprising a light diffusing sample chamber 400 and comparison of the data to identify discriminating features of each embryo group for use in embryo classification.

Methods:

Embryo Samples:

A total of 160 Loblolly pine embryos from six embryo groups were imaged. The six embryo groups included three different somatic genotypes and zygotic embryos which differed in prior culture conditions and/or storage methods as shown below in TABLE 1.

Loblolly pine (*Pinus taeda*) somatic embryos were generated using standard conditions as described in Example 1 of U.S. patent application Ser. No. 10/394,549, incorporated herein by reference. As described, female gametophytes containing zygotic embryos were removed from seeds four to five weeks after fertilization and subjected to a multiple step process including stage I: induction; stage II: maintenance and multiplication; stage III: embryo development. After development (stage III), the embryos were treated as shown in TABLE 1 prior to imaging.

Loblolly pine mature zygotic embryos were obtained from seeds collected in the fall and stored in the freezer. Seeds were obtained from freezer storage, and the decoated seed allowed to imbibe water for 14 hours before extraction of the embryos for analysis. Cones and seed were stored at 4-6° C. after collection until spectral analysis was performed.

TABLE 1

Summary of Embryo Samples

| Group # | Genotype | Culture history | No. of Embryos imaged |
|---|---|---|---|
| 1 | zygotic | from freezer, imbibed, dissected and stored for 10 weeks at 1° C. prior to imaging | 16 |
| 2 | A (somatic) | after development stage transferred to hormone free medium and stored for 10 weeks at 1° C. before imaging | 20 |
| 3 | B (somatic) | after development stage, transferred to hormone free medium and stored for 10 weeks at 1° C. prior to imaging | 22 |
| 4 | zygotic (same source as group 1) | imbibed and dissected fresh from the freezer prior to imaging (no storage time) | 33 |
| 5 | A (somatic) | after 12 weeks of development, maintained on development media at 4-6° C. prior to imaging | 34 |
| 6 | C (somatic) | after development, conditioned on a membrane over water prior to imaging | 35 |

Hyperspectral Line Image Measurement Procedure:

Using the imaging system 300 described in EXAMPLE 2, hyperspectral line images were obtained of a total of 160 embryos from the 6 different types as shown in TABLE 1 over a time period of two days. Images of embryos from Groups 1-3 were obtained on the first day and images of embryos from Groups 4-6 were obtained on the second day.

The procedure for obtaining the images was as follows. After an initial 30-minute instrument warm up period with the lamp on, a background set of 64 images was taken at 100 msec/image on a clean area of the sample platform. Another set of dark current images were taken of the same spot of the sample platform with the illumination turned off.

The first embryo from Group 1 was imaged, followed by the first from Group 2, the first from Group 3. This was repeated for 3 embryos from each group, then followed by another background set of images. The average of the before and after background image sets were used as the reference base for the 12 embryos in between. On average, it took about 90 seconds per embryo to load the embryo into the target area, image the embryo, and save the image.

Each time an embryo was placed on the surface of the specimen platform, a pristine spot on the background piece of Gore-Tex® (e.g., a spot free of previous embryo debris or dents) was chosen. Dark current images varied much less than white background images and were therefore acquired at less frequent intervals. When pristine spots were not readily available, a fresh background piece. (approx. 8×8 cm) of Gore-Tex® was cut and fastened to the platform.

The imaging system 300 was set up and operated as described in EXAMPLE 2. Each embryo was positioned into the target area such that the embryo's longitudinal axis 16 (shown in FIG. 4A) was aligned with the monochromator slit 142, to obtain a complete spectrum for each pixel in a single line of pixels along the longitudinal axis of the embryo. 64 frames of each embryo or background image were obtained and averaged to produce a single image.

Figure 4B:
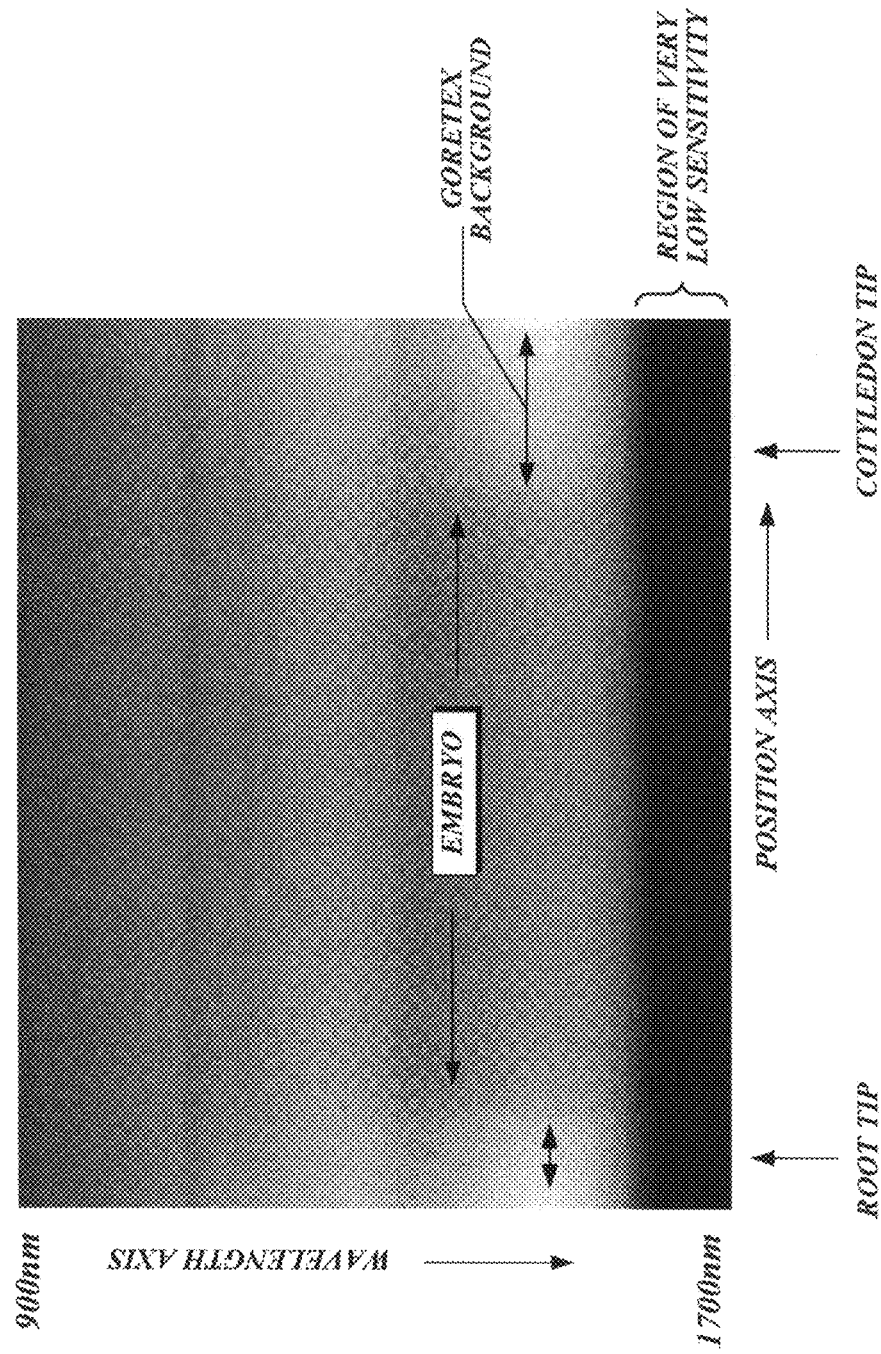
FIG. 4B illustrates a raw screen image obtained of an embryo 8 using the imaging system 300 in accordance with an embodiment of the invention.

FIG. 4B illustrates a raw computer screen image obtained of a single-pixel line along the longitudinal axis of an exemplary embryo 8 using the imaging system 300. As shown in FIG. 4B, the NIR spectrum (900 nm to 1700 nm) (shown as the y axis) was obtained for each pixel along the longitudinal axis of the embryo (shown as the x axis, scale=5 mm) from the root tip at position=0, to the cotyledon tip at position=1. The position of the embryo was either expressed in terms of pixels from 1-300, or as a fraction of the total length. As further shown in FIG. 4B, the positions of the embryo (darker area) and the Gore-Tex® background (lighter areas to the right and left of the embryo) are indicated.

Image Analysis:

The 64 frames of each embryo or background image were averaged to produce a single image. This step reduced the noise to about one-fifth of that between individual frames, as measured by averaged pixel to corresponding pixel standard deviation across frames. Dark current images were also averaged. The data was then standardized with respect to background by dividing the resulting embryo image (minus dark current image) by the resulting background image (minus dark current image) to give a single 3D spectral reflectance image of each embryo scaled from position 0 to 1.

To allow for ease of comparison between embryos and embryo groups, differences in embryo length were eliminated by expressing position along the embryo as a fraction of its total length from root cap (position=0) to cotyledon tip (positional). The end position was approximated by the point at which there was a distinct change in spectral variance between embryo and background at either end. Individual-embryo plots of position effect (at selected wavelengths) and spectra (at various positions) could then be compared.

Figure 5A:
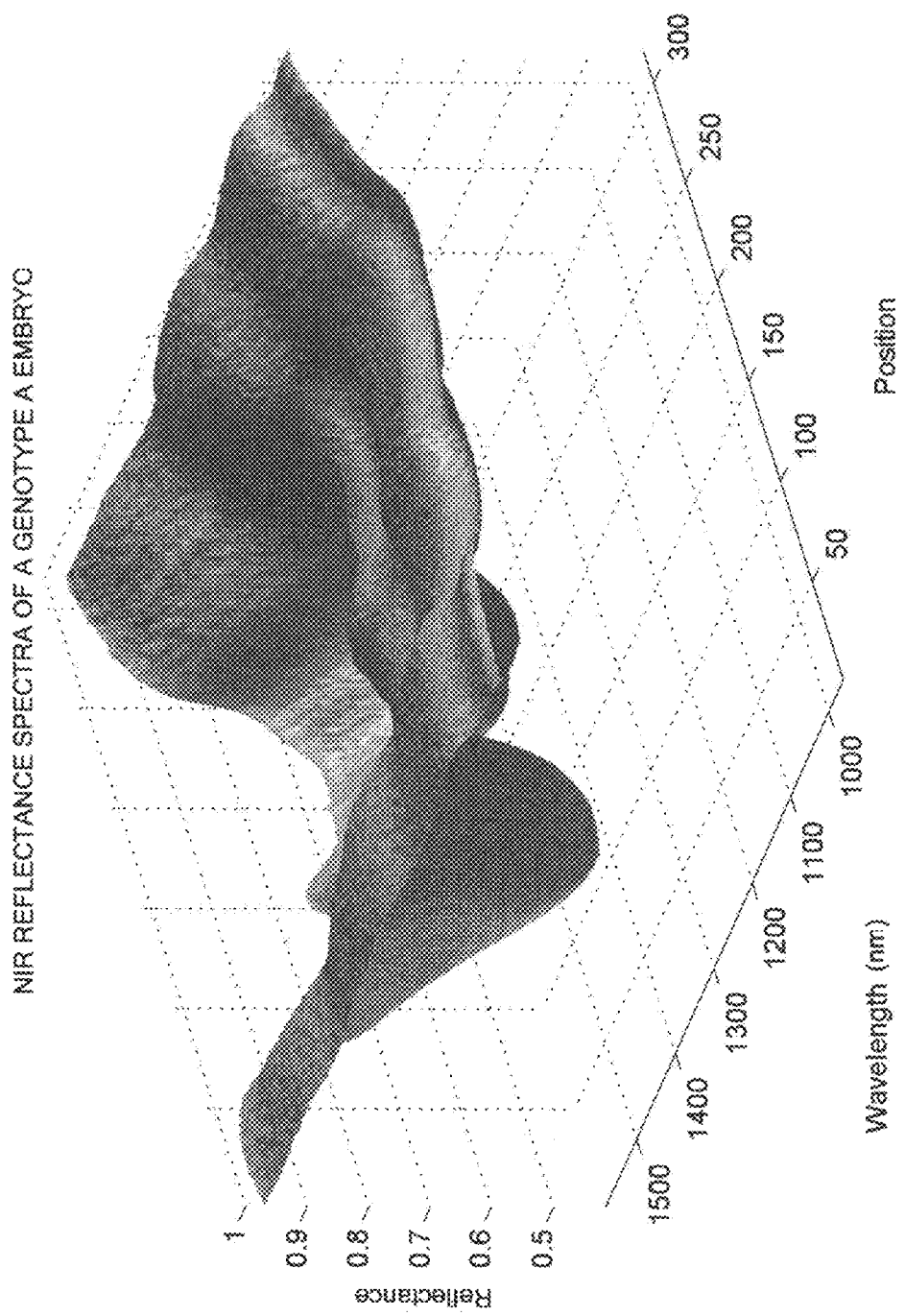
FIG. 5A graphically illustrates a 3D view of a corrected image profile obtained from a single 100-millisecond exposure of an embryo of Genotype B in which reflectance of NIR light is the vertical axis and wavelength (nm) and position along the embryo's longitudinal axis (in number of pixels) are the horizontal axes.

To illustrate the differences in the surface topography among groups, the re-scaled 3D images were averaged for the 16-35 embryos within each group. FIG. 5A shows an exemplary 3D graphical view of a corrected image (corrected for background) from Group 3 (genotype B) embryos in which reflectance of NIR light is the vertical axis and wavelength (in nm) and position along the embryo axis (in number of pixels from 1-300) are the horizontal axes. It is noted that FIG. 5A is a single image and is not the average of a plurality of images.

Figure 5B:
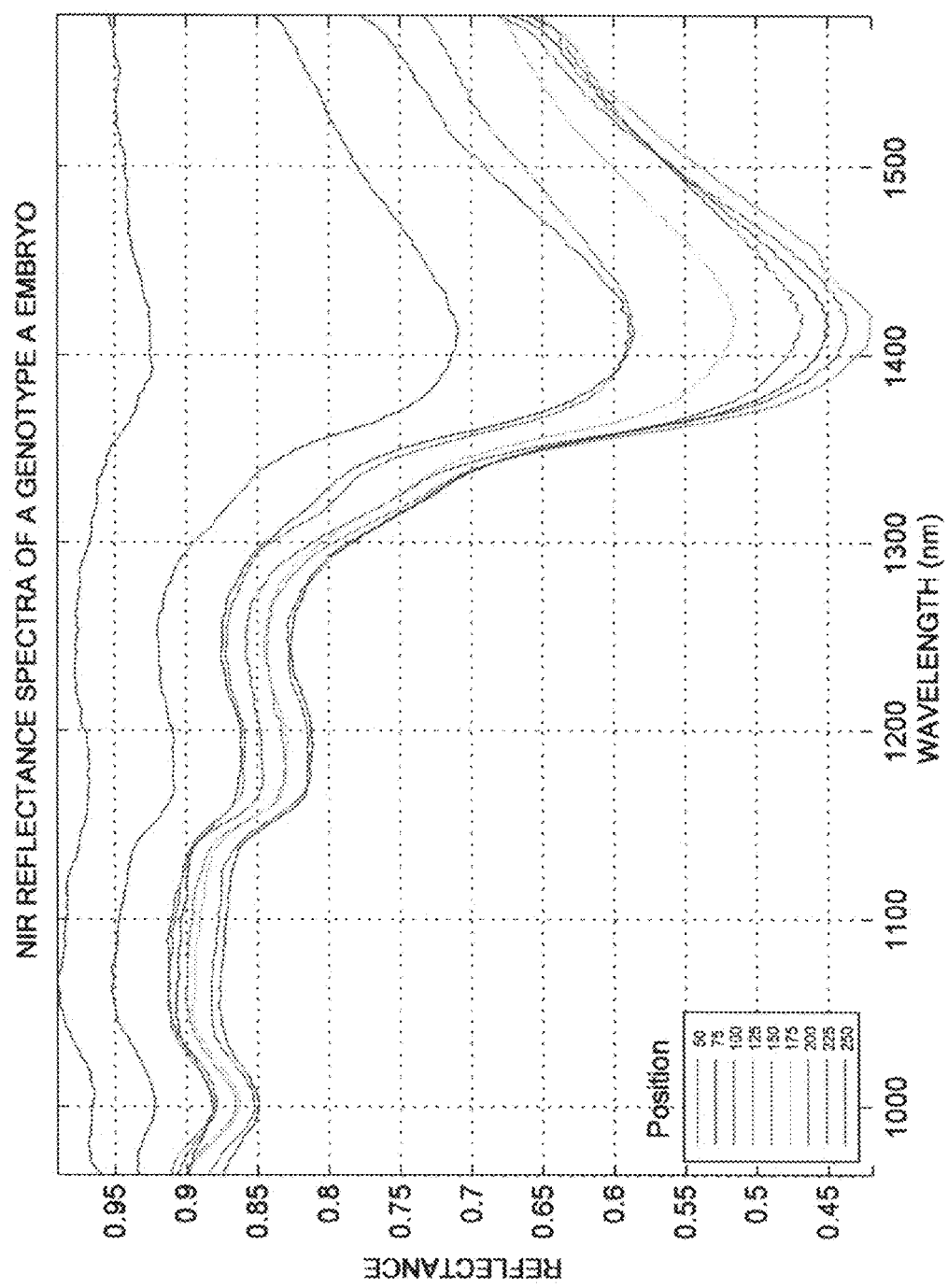
FIG. 5B graphically illustrates nine NIR reflectance spectra at selected positions along the averaged image from 64 video frames of the embryo shown in FIG. 5A.

FIG. 5B graphically illustrates nine NIR reflectance spectra at selected positions along the averaged image from 64 video frames of the embryo shown in FIG. 5A.

Figure 5C:
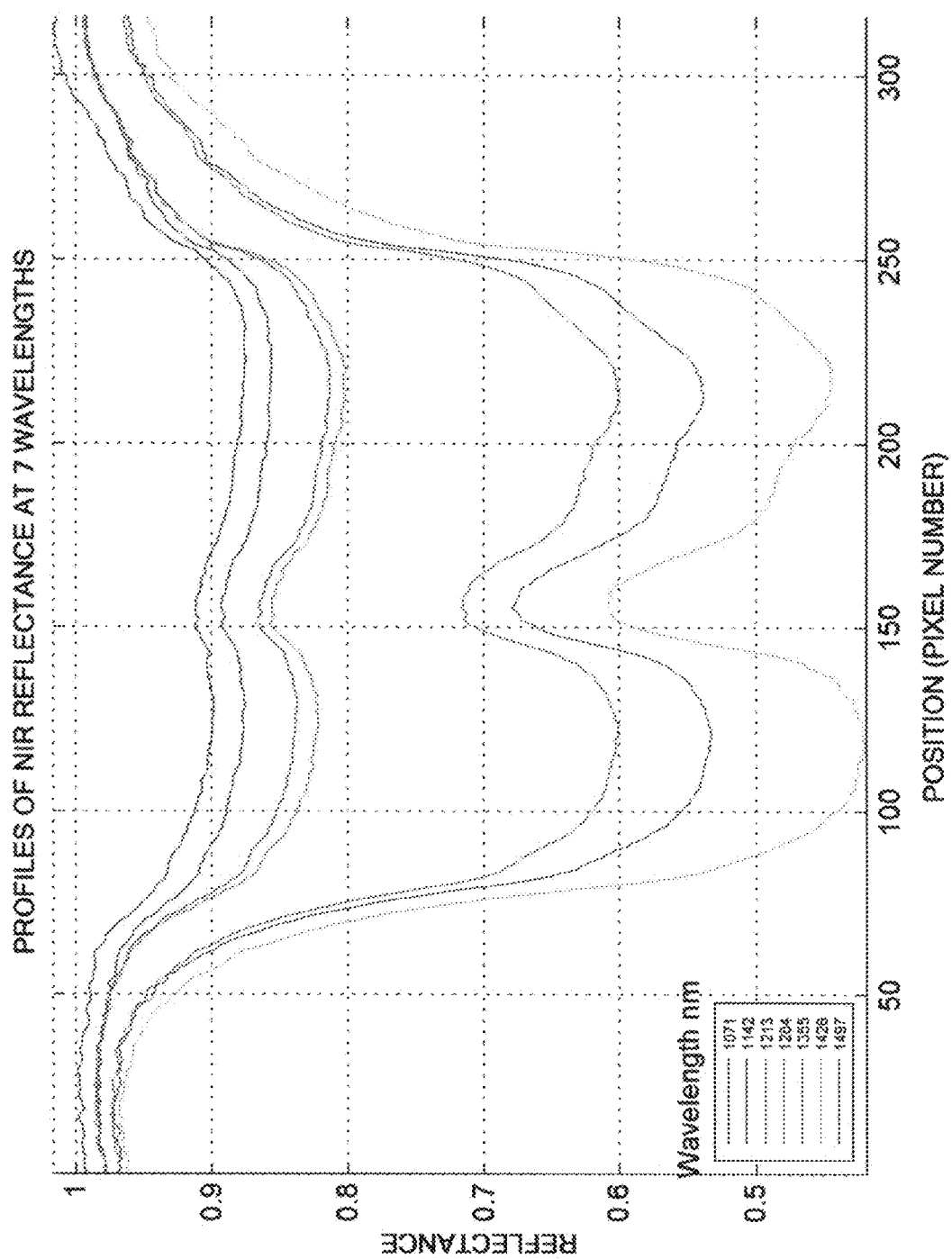
FIG. 5C graphically illustrates seven profiles of NIR reflectance at different positions along the embryo's longitudinal axis line at selected NIR wavelengths from FIG. 5A.

FIG. 5C graphically illustrates seven profiles of NIR reflectance at different positions along the embryo's longitudinal axis line at selected NIR wavelengths from FIG. 5A.

It can be seen that the spectra in FIG. 5B are of a generally similar shape for all positions along this embryo, except for the one position closest to the root tip (position 50), which reflects much more light at all wavelengths presumably because this is the tissue through which reflection from the background Gore-Tex® predominates over adsorption by the tissue itself. The spectra at all other positions along the embryo match those previously obtained from whole embryos using a Fieldspec spectrometer in a different study (data not shown), demonstrating that the imaging system 300 was generating reliable image data.

Comparison of Image Data from the 6 Different Embryo Groups

As described above, the hyperspectral line images (HLI) from each of the 16-35 embryos per group (shown in TABLE 1) were averaged to obtain a single HLI for each group. The mean images for each group were graphed in 3D and 2D images and compared (not shown).

A comparison of the profiles showed the importance of positional information in allowing the groups of embryos to be separated.

For example, it was determined that zygotic embryos (e.g., Group 4) could be best distinguished from the somatic embryos (e.g., Group 3) by the difference in reflectance of the embryos around the base of the cotyledons (70-80% of the distance up from the root tip).

In another example, it was determined that Genotype B somatic embryos (Group 3) could be best distinguished from Genotype C somatic embryos (Group 6) by the difference in reflectance of the embryos in the mid-hypocotyl region.

Statistical Significance

The individual embryo images were used to calculate Smirnov statistics and t-tests for each combination of position and wavelength. The statistical significance of the tests comparing groups was determined by using re-sampling methods on the individual images. To test for statistical significance, the embryo group labels were randomly reallocated to the embryo images, and the t-statistics or Smirnov statistic was recalculated based on the new group assignments.

Under the hypothesis that there are no group differences, randomly re-labeling the embryos should produce t- and Smirnov statistics that are similar in magnitude to those calculated with the correct labeling. Smirnov statistics, like t-tests and F-tests, measure the difference between two distributions. While t-tests measure the difference between the means and F-tests measure the difference between the variances, the Smirnov statistic measures how much two distributions overlap. If two distributions match perfectly, then the statistic has a value of 0. On the other hand, if the two distributions do not overlap at all, then the statistic has a value of 1. The Smirnov statistic was chosen among several other overlap statistics because it is more sensitive to overlaps caused by means and is relatively simple and easy to interpret.

The embryo images were randomly re-labeled 1000 times to produce histograms of values against which the statistics based on the correct labeling were compared. If the statistics based on the correctly labeled embryos are located in the tails of the histograms, or far from the histograms, then they were judged to be significant.

The Smirnov statistics and t-test results were graphed in a series of Statistical Parametric Maps in contrast colors to determine either positive (blue areas) or negative (yellow areas) in the maps that indicate statistically significant differences (t-test maps not shown).

Smirnov values show positions and wavelengths where distributions of NIR reflectance values show relatively little overlap between the two groups and are shown in blue. In the case of the Smirnov statistics, the test statistics can only be positive, therefore the bright blue indicated wavelength-by-position combinations where the distributions of the NIR values were significantly different. Once the results were plotted, the contour lines in the plots showed the location of the actual boundary between significant and non-significant areas. Areas on the blue side of the Smirnov contour lines are where significant differences exist.

Results of Statistical Analysis:

Examination of the maps revealed significant areas with "island," "bay," "peninsula," and "curved coastline" shapes. As described above, such shapes are proof of the existence of wavelength by position interactions when using the NIR hyperspectral line images to discriminate between groups of embryos.

Figure 6:
FIG. 6 is a representative contrast map of Smirnov values showing a contrast identified as "X" between embryos of Group 6 and embryos of Group 5. High Smirnov values (high values shown in blue) show positions and wavelengths where distributions of NIR reflectance values show relatively little overlap between the two groups; therefore, separation of the two groups based on wavelength-by-position data at these coordinates results in a higher degree of purity of separation.

FIG. 6 shows an exemplary contrast map (X) of Smirnov values between Group 6 embryos and Group 5 embryos. High Smirnov values (high values shown in blue in FIG. 6) show positions and wavelengths where distributions of NIR reflectance values show relatively little overlap between the two groups, therefore separation of the two groups based on wavelength-by-position data at these coordinates results in a higher degree of purity of separation. As shown in FIG. 6, only small islands of statistical significance were observed, therefore it seems likely that no difference between these groups would have been detectable using a single-patch embryo spectrum, which only measures NIR spectra from a much larger circular region on a portion of an embryo.

A contrast map (Y) of Smirnov values between Group 6 and Group 3 showed statistically significant differences across all the NIR wavelengths (contrast map not shown).

A contrast map (Z) of Smirnov values between Group 4 (zygotic) and Group 3 (somatic genotype B) showed the greatest difference in values with respect to the absolute magnitude of the t-test values (>15) and the Smirnov values (>0.9), as well as with respect to the large coverage of both wavelength and positional axis ranges (contrast map not shown). In the comparison of these two groups, it appears that a single spectrum would likely have detected a difference between groups. However, even in the comparison of these two groups (Group 4 vs. Group 3), by selecting combinations of particular wavelengths and positions, more accurate discrimination would likely be achievable using the hyperspectral data.

These results demonstrate that hyperspectral line image data can be used to distinguish between various types of embryos, including different genotypes of Loblolly pine somatic embryos; and zygotic versus somatic conifer embryos. As further described in Example 6, wavelength-by-position data can also be used to distinguish embryos with high conversion potential (i.e., high germination frequency) from embryos with low conversion potential. Therefore, the use of hyperspectral line image data provides an advantage over single spectra obtained from a circular view of a portion of an embryo (referred to as "single-patch spectra") such as obtained from a FieldSpec instrument, which cannot detect such wavelength-by-position interactions.

Principal Component Analysis (PCA)

Principal component analysis (PCA) was carried out on the statistically significant NIR wavelength-by-position data. It was further determined whether statistically significant differences observed between the different embryo groups as described above would be large or consistent enough to allow for useful separation of groups of embryos using a single classification model. Due to the small sample sizes, the degree of separation between groups was assessed visually by examining labeled scatterplots constructed from the three most effective PCs.

Figure 7A:
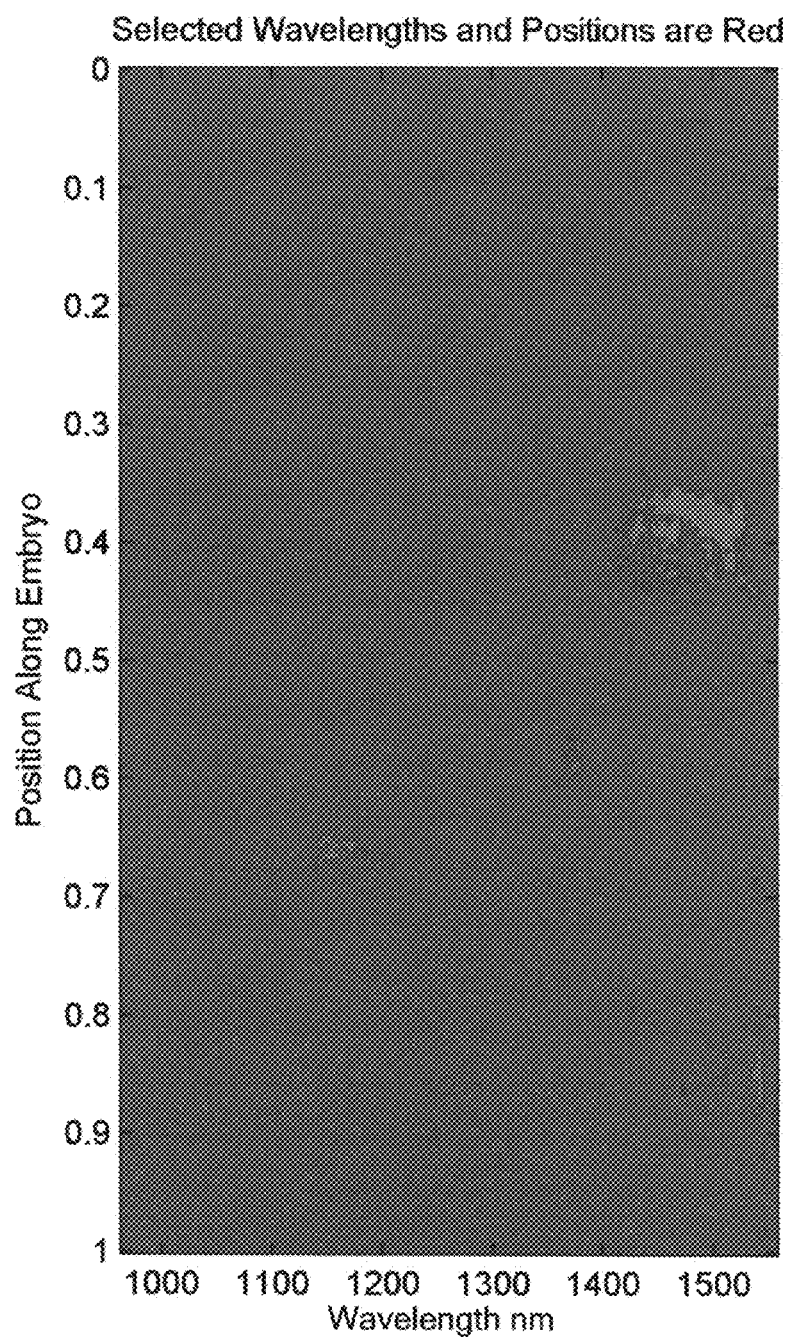
FIG. 7A graphically displays embryo position X wavelength coordinates that were found to be common to statistically significant differences between any two embryo groups of six embryo groups analyzed (including 3 different genotypes of somatic embryo groups and two zygotic embryo groups as shown in TABLE 1)
Figure 7B:
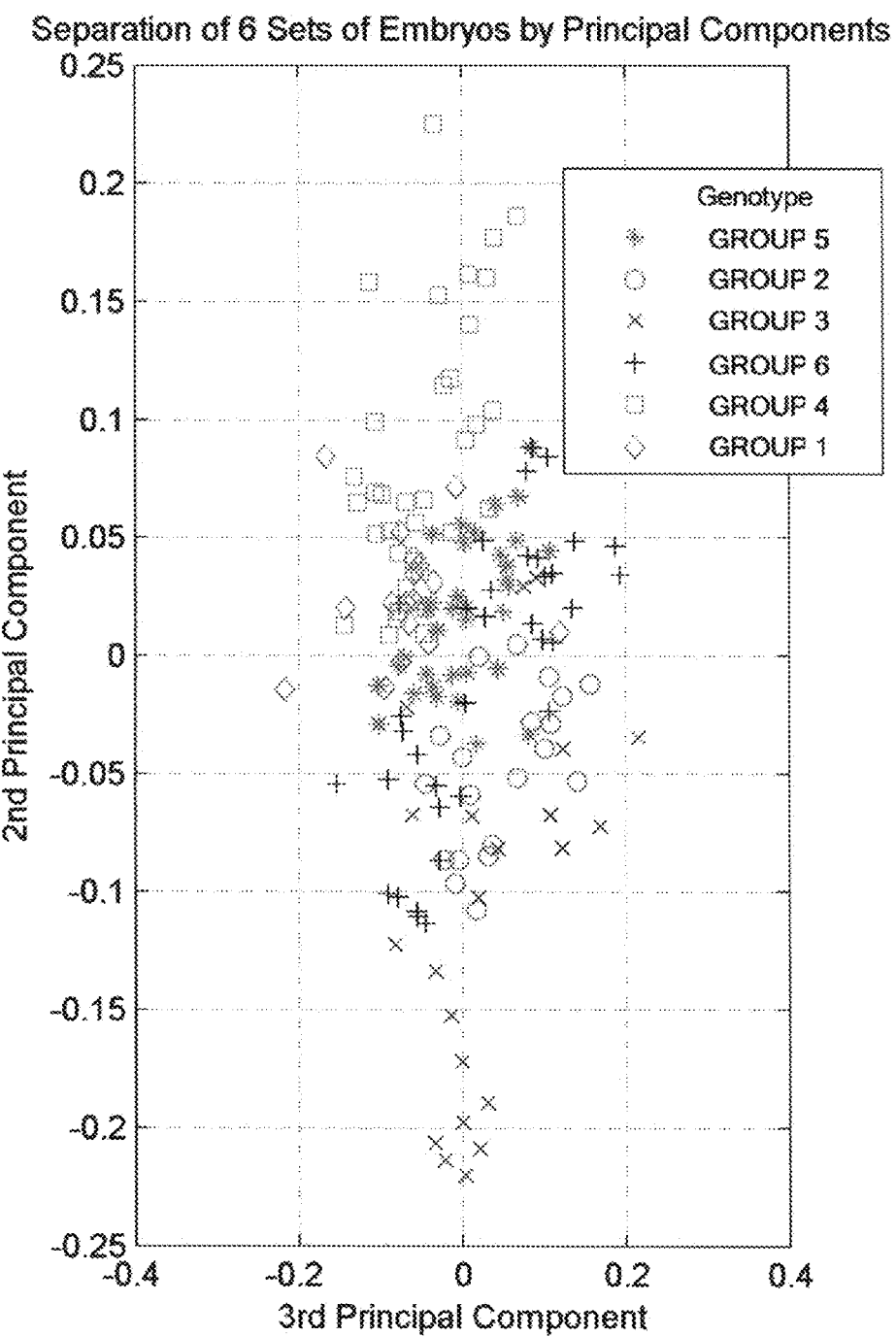
FIG. 7B displays a score plot obtained from a principal component analysis utilizing all variables falling within the significant coordinate areas shown in FIG. 7A.

The principal component analysis was first achieved by identifying those position and wavelength combinations from the contrast maps that always contributed significantly to discrimination, no matter which group was compared with which. FIG. 7A displays embryo wavelength-by-position coordinates that were found to be common to statistically significant differences between any two embryo groups of six embryo groups tested (including three different somatic embryo genotypes and zygotic embryos, with reference to the groups designated in TABLE 1). All the wavelength-by-position variables contained in these identified common areas were then included in a principal component analysis. The "score plot" of the two principal components accounting for most of the variance between groups is shown in FIG. 7B. As shown in FIG. 7B, it is possible to clearly or partially separate groups of embryos from one another based on the limited numbers of embryos imaged from each group. For example, it is apparent from FIG. 7B that both cold-stored (Group 1) and freshly excised (Group 4) zygotic embryos can be completely separated from stored somatic embryos of Genotype B (Group 3) and Genotype A (Group 5) (as compared in contrast Z described above). As another example, it is apparent from FIG. 7B that approximately 60% of Genotype B embryos (Group 3) could be separated as a pure group from Genotype A embryos (Group 5), and that, while the distributions of Genotype A (Group 5) and Genotype C (Group 6) may have differed significantly by the Smirnov test, only a low accuracy separation of them could have been achieved (as compared in contrast X described above). From these results it is apparent to one skilled in the art that separate classification models can be constructed using routine methods known to those of skill in the art to select any particular group from other groups with a useful level of accuracy.

Overall Summary of Results:

These results demonstrate that hyperspectral line image data can be used to distinguish between types of embryos, including zygotic versus somatic embryos, somatic embryos of different genotypes, and embryos of the same genotype that have been produced using different culture conditions. As described in more detail in Example 6, the use of wavelength-by-position data can also be used to distinguish between embryos with high and low germination potential. These results therefore demonstrate the importance of positional information to enhance effectiveness of NIR (chemical) discrimination between different embryo groups.

EXAMPLE 5

This Example demonstrates that the use of wavelength-by-position data obtained from hyperspectral line imaging of embryos allows for an increased accuracy in classifying embryos in comparison to the use of wavelength data alone.

Methods:

Three different spectral data sets were obtained from the embryos described in TABLE 1 in Example 4: (1) a "wavelength-by-position" data set as described in Example 4; (2) a "wavelength only" data set which was the 250 spectra for each embryo obtained as described in EXAMPLE 4, averaged to produce a single spectrum for the viewed axial line; and (3) a "position only" data set which was created using the average NIR reflectance (i.e., the average of all NIR wavelengths from 900-1680 nm) of each position on the axial line imaged on the embryo.

Principal Component Analysis:

For the "wavelength only" data set, a principal component analysis was run using all 500 wavelength values for each embryo as the input.

For the "position only" data set, a principal component analysis was run using all 250 position values per embryo.

For the "wavelength-by-position" data set, the 250×500 per embryo matrix was reduced to a manageable size by choosing only those positions and wavelengths which, for at least one of the 15 possible group contrasts, had a high absolute t-value or a high value of the Smirnov statistic, determined as described in Example 4.

Figure 8A:
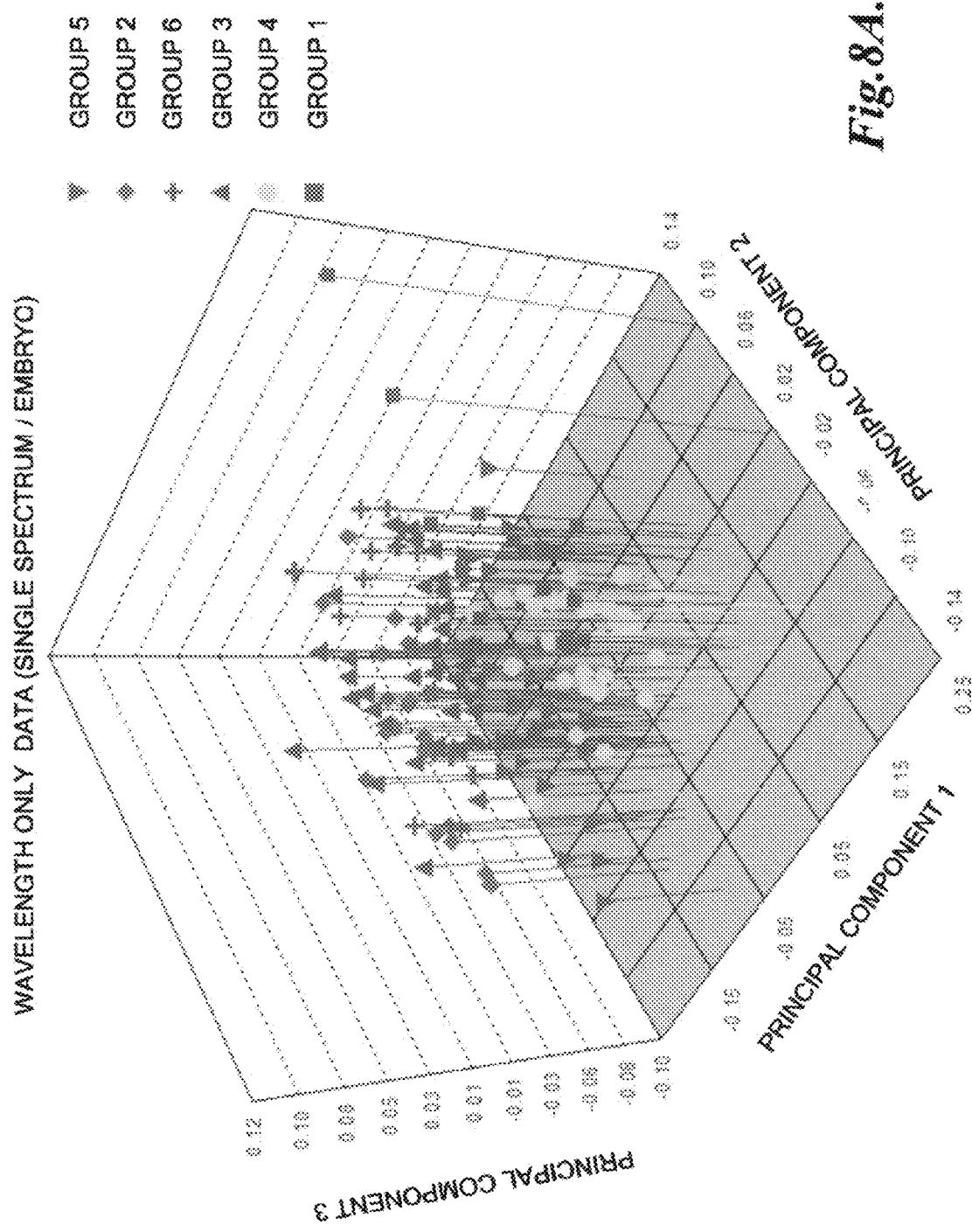
FIG. 8A graphically illustrates a three-principal component analysis of the wavelength only (control) data set (data shown is the average of 250 NIR spectra/embryo) of the embryos from the six embryo groups designated with reference to TABLE 1.

Results:

FIG. 8A graphically illustrates a three-principal component analysis of the wavelength only (control) data set (data shown is the average of 250 NIR spectra/embryo) along the axial line on embryos from the six embryo groups designated with reference to TABLE 1.

Figure 8B:
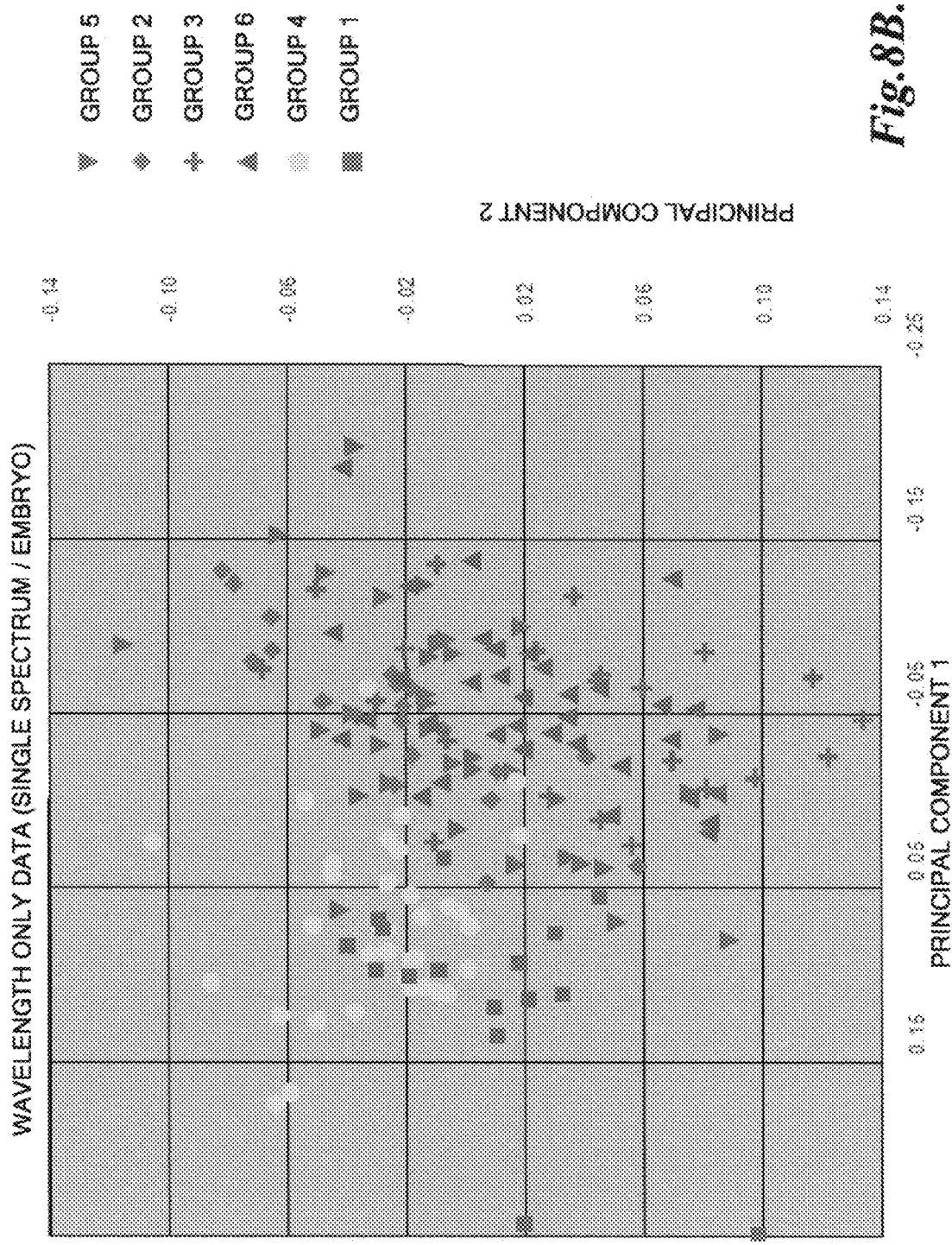
FIG. 8B graphically illustrates a two-principal component analysis of the wavelength only data set (data shown is the average of 250 NIR spectra/embryo) of the embryos from the six embryo groups designated with reference to TABLE 1.

FIG. 8B graphically illustrates a two-principal component analysis of the wavelength only data set (data shown is the average of 250 NIR spectra/embryo) along the axial line on embryos from the six embryo groups designated with reference to TABLE 1.

Figure 8C:
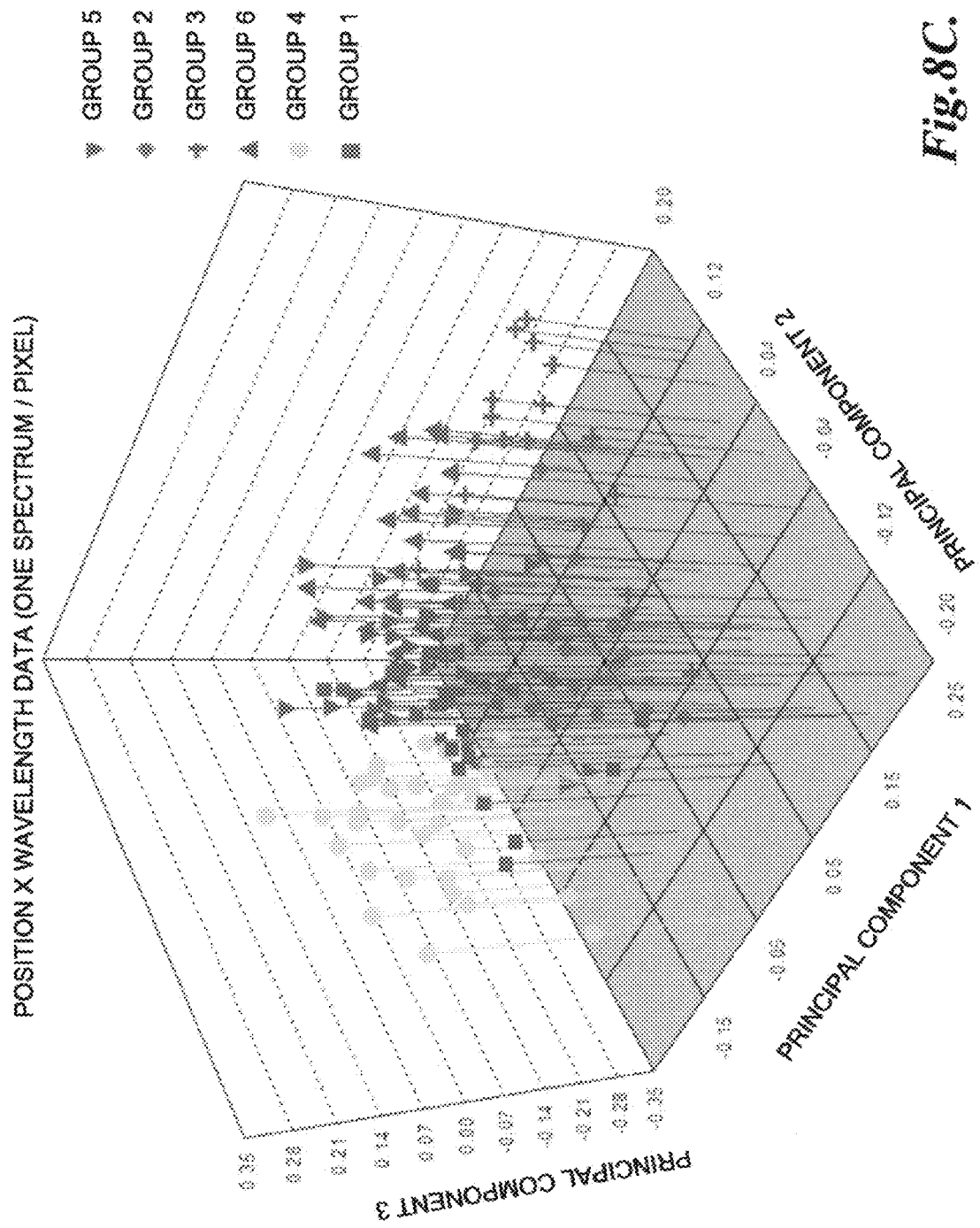
FIG. 8C graphically illustrates a three-principal component analysis of the wavelength-by-position data set based on 250 separate spectra along each embryo (one spectrum/pixel) of the embryos from the six embryo groups designated with reference to TABLE 1.

FIG. 8C graphically illustrates a three-principal component analysis of the wavelength-by-position data set based on 250 separate spectra along the axial line on each embryo (one spectrum/pixel) of the embryos from the six embryo groups designated with reference to TABLE 1.

Figure 8D:
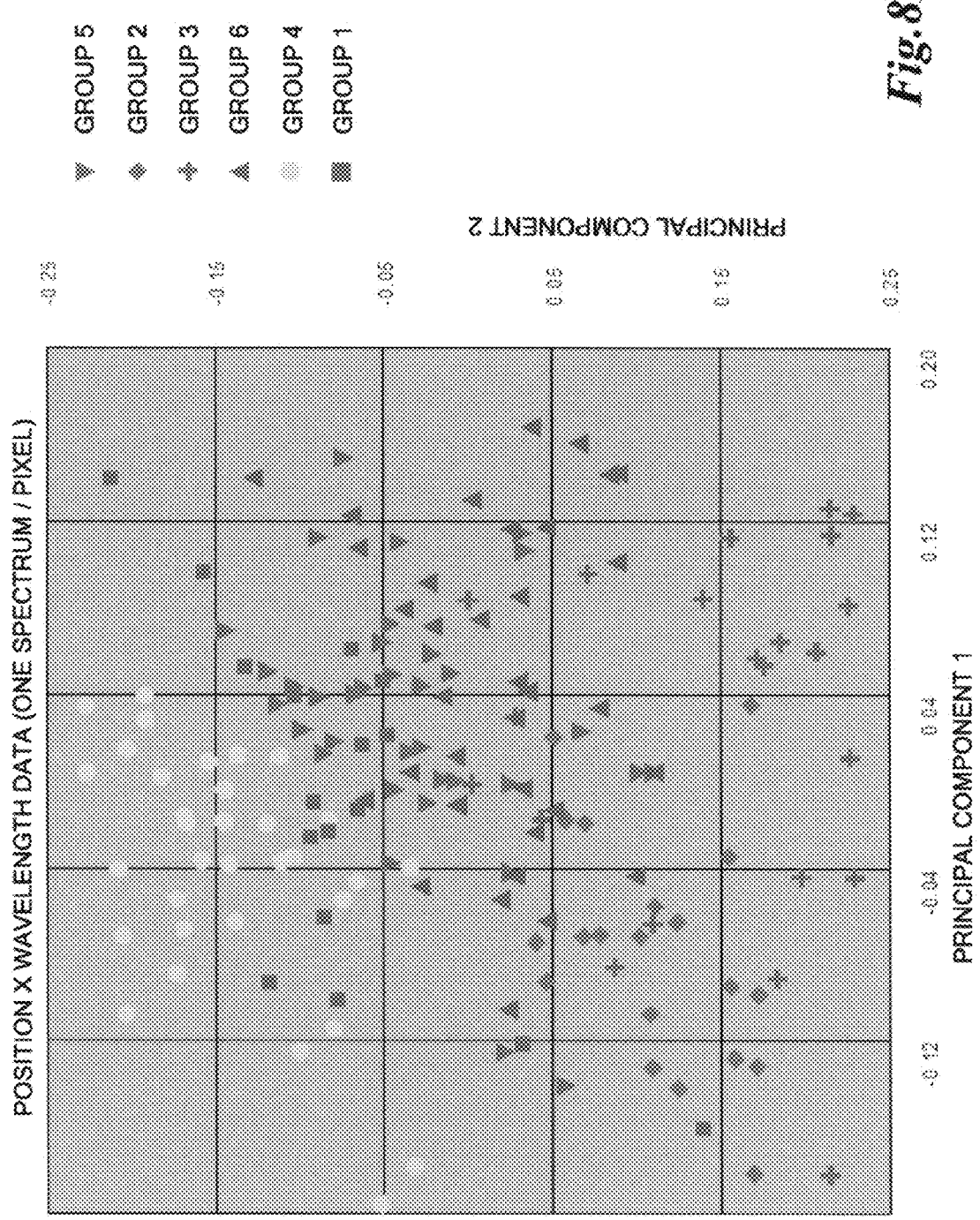
FIG. 8D graphically illustrates a two-principal component analysis of the wavelength-by-position data set (one spectrum/pixel) embryos from the six embryo groups designated with reference to TABLE 1.

FIG. 8D graphically illustrates a two-principal component analysis of the wavelength-by-position data set (one spectrum/pixel) along the axial line on embryos from the six embryo groups designated with reference to TABLE 1.

Figure 9A:
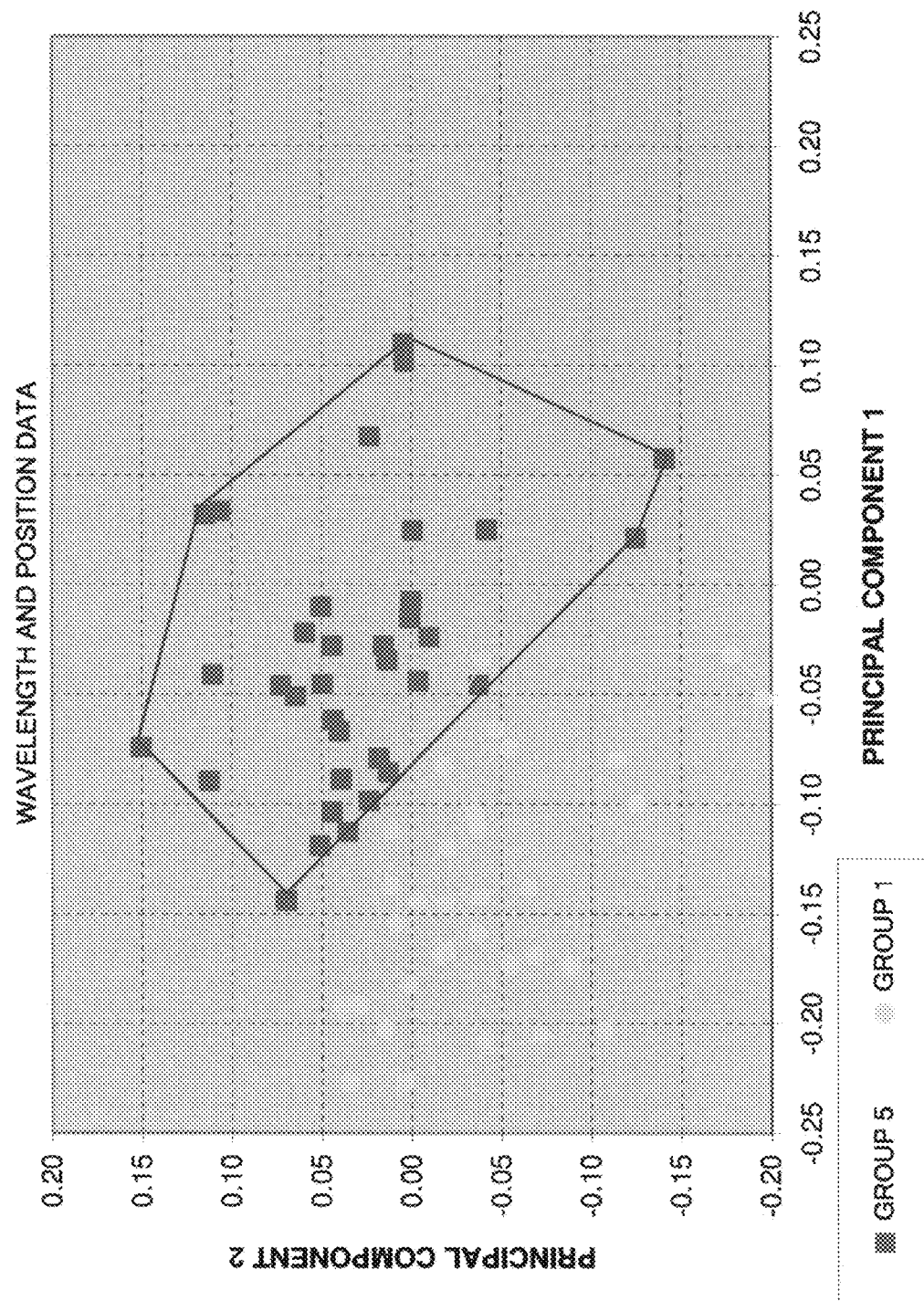
FIG. 9A graphically illustrates an exemplary principal component score plot derived from wavelength-by-position data contrasting Group 5 and Group 1, with convex hulls drawn to allow counts of the number of overlapping points, which provides a measure of potential classification error.
Figure 9B:
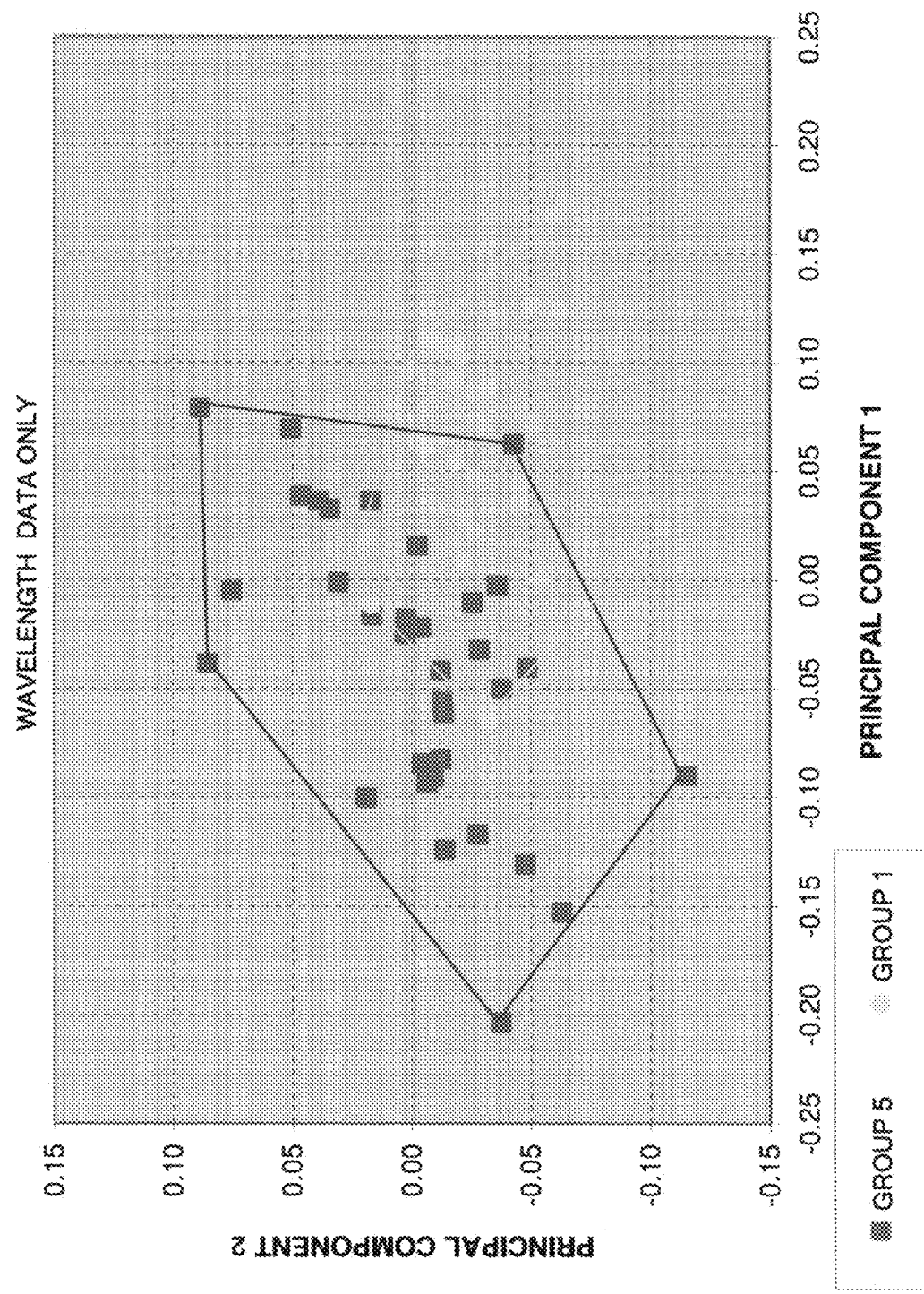
FIG. 9B graphically illustrates a principal component score plot contrasting Group 5 and Group 1 using only wavelength data, with convex hulls drawn to allow counts of the number of overlapping points.

The results shown in FIGS. 8A-D demonstrate that the use of wavelength-by-position data allowed better discrimination among the six embryo groups than was obtainable from the wavelength data alone. To further quantify the extent of this improvement, each of the 15 possible contrasts of groups shown in TABLE 1 was score-plotted separately, and a convex hull was drawn around each. A convex hull is a line connecting the outermost points in a group and enclosing all the other points, with no internal angles >180°. An example of a convex hull of a contrast group plotted using wavelength-by-position is shown in FIG. 9A, and a convex hull of the same contrast group plotted using wavelength only data is shown in FIG. 9B. The number of embryos (data points) in the convex hull overlap was divided by the total number in the pair to give a measure of "classification error." The results for the 15 contrasts between the groups shown in TABLE 1 using the convex hull analysis are provided in TABLE 2 below.

TABLE 2

Comparison of convex hull overlaps as a measurement of misclassification (classification errors) for 15 different group contrasts using three data sets as a basis for discrimination between the groups.

| Contrast Groups (with reference to TABLE 1) | Total number of Embryos | Convex hull overlap (%) Wavelength × Position[1] | Wavelength only | Position only | Result Improved by hyperspectral imaging? |
|---|---|---|---|---|---|
| Group 5 v. Group 2 | 55 | 0 | 0 | 22 | Equal |
| Group 5 v. Group 3 | 57 | 14 | 23 | 30 | Yes |
| Group 5 v. Group 6 | 70 | 33 | 33 | 89 | Equal |
| Group 5 v. Group 4 | 68 | 3 | 37 | 41 | Yes |
| Group 5 v. Group 1 | 51 | 0 | 4 | 67 | Yes |
| Group 5 v. Group 3 | 42 | 36 | 48 | 36 | Yes |
| Group 5 v. Group 6 | 55 | 15 | 40 | 22 | Yes |
| Group 5 v. Group 4 | 53 | 0 | 0 | 8 | Yes (greater distance between non-overlapping hulls) |
| Group 5 v. Group 1 | 36 | 0 | 0 | 39 | Yes (non-overlap on all 3 PC axes versus 2 PC axes) |
| Group 3 v. Group 6 | 57 | 25 | 70 | 25 | Yes |
| Group 3 v. Group 4 | 55 | 0 | 0 | 4 | Yes (greater distance between non-overlapping hulls) |
| Group 3 v. Group 1 | 38 | 0 | 0 | 18 | Equal |
| Group 6 v. Group 4 | 68 | 0 | 7 | 41 | Yes |
| Group 6 v. Group 1 | 51 | 0 | 0 | 41 | Equal |
| Group 4 v. Group 1 | 49 | 33 | 33 | 37 | Equal |
| Average misclassification | | 10 | 20 | 35 | 10 improved (out of 15) |

[1]Note this category also includes "wavelength only" and "position only" results because each can be derived from the wavelength × position data.

As described above in TABLE 2, in three of the contrast groups, there was zero convex hull overlap, either in wavelength-only or wavelength-by-position plots. However, based on a greater distance between the 100% pure groups, or separation in an additional PC dimension, the wavelength-by-position plots were still considered to be improvements over wavelength-only data.

Therefore, in summary, 10 of the 15 classification contrasts were improved by the use of the hyperspectral line imaging method (wavelength-by-position) and the remaining 5 classification contrasts were at least as good as the wavelength-only method. The results shown in TABLE 2 indicate that the average misclassification rate was halved (from 20% to 10%) using hyperspectral line imaging (wavelength-by-position) versus single-spectrum data, which was a statistically significant result (p=0.028 by paired t-test). This result is the equivalent of raising the average purity of a group from 80% to 90%, which is a highly worthwhile outcome, especially if used to distinguish between embryos that have a high versus low conversion potential (i.e., predictive for germination frequency and vigor).

In comparison, the average NIR reflectance value from "position only" obtained at 250 positions (i.e., no spectral information) provided discrimination at 65% group purity, which is significantly lower, but may also be useful for separation of embryos under some circumstances.

The results of this Example demonstrate the feasibility and value of using NIR hyperspectral line imaging for embryo selection. The data collected demonstrate that various types of somatic and zygotic embryos can be completely or partially distinguished from one another based on the wavelength-by-position data, and that this discrimination is significantly better (approximately 90% accurate on average) than discrimination based on wavelength measurements alone (approximately 80% accurate) or position measurements alone (approximately 65% accurate). In other words, hyperspectral line imaging "sees" chemical differences in embryos better than wavelength-only imaging. These results further demonstrate the importance of positional information to enhance effectiveness of NIR (chemical) discrimination between different embryo groups.

EXAMPLE 6

This Example demonstrates that the use of wavelength-by-position data obtained from standard NIR spectroscopy at only two positions on the embryo allows for improved discrimination between embryos with high and low germination potential (i.e., high or low conversion frequency).

Methods:

Standard spectroscopy analysis was carried out on 345 Loblolly pine embryos of Genotype D using the methods described in co-pending U.S. patent application Ser. No. 11/836,095, incorporated herein by reference. Briefly described, spectra were taken from both the cotyledon region of an embryo (i.e., from 0.5 to 1.0 shown in FIG. 4A) and the root-end of the embryo (i.e., from 0 to 0.5 shown in FIG. 4A) under sterile conditions.

The experimental setup consisted of a light source, a binocular microscope, a NIR sensor, and a portable NIR processor with computer. A FieldSpec FR (350-2500 nm) Spectrometer (Analytical Spectral Devices, Inc., Boulder Colo.) equipped with a fiber optic probe which gathers light reflected from any surface was used to collect embryo spectral data.

The fiber optic probe of the spectrometer was fitted with a 5 degree fore-optic and inserted into the auxiliary observation (camera) port of a binocular microscope.

Spectra were acquired sequentially from groups of ten somatic embryos immediately after hand-transferring from a culture plate. The halogen lamp was set at 40 degree angle from the vertical at a distance of 17 cm from the embryos. Samples were placed on a white Teflon surface to minimize background absorption while being viewed with the 6.5×, 10×, or 40× microscope objective. A "white balance" program that is part of the spectrometer was run periodically throughout the measurements to recalibrate the instrument against the white background when no embryos were present. Spectra were measured in the region from visible to near IR range (400 to 2500 m). Spectral intensities were measured at 1 nm increments.

After spectral evaluation, the 345 Loblolly pine embryos of Genotype D were germinated and the spectral analysis was compared to germination success.

Figure 10:
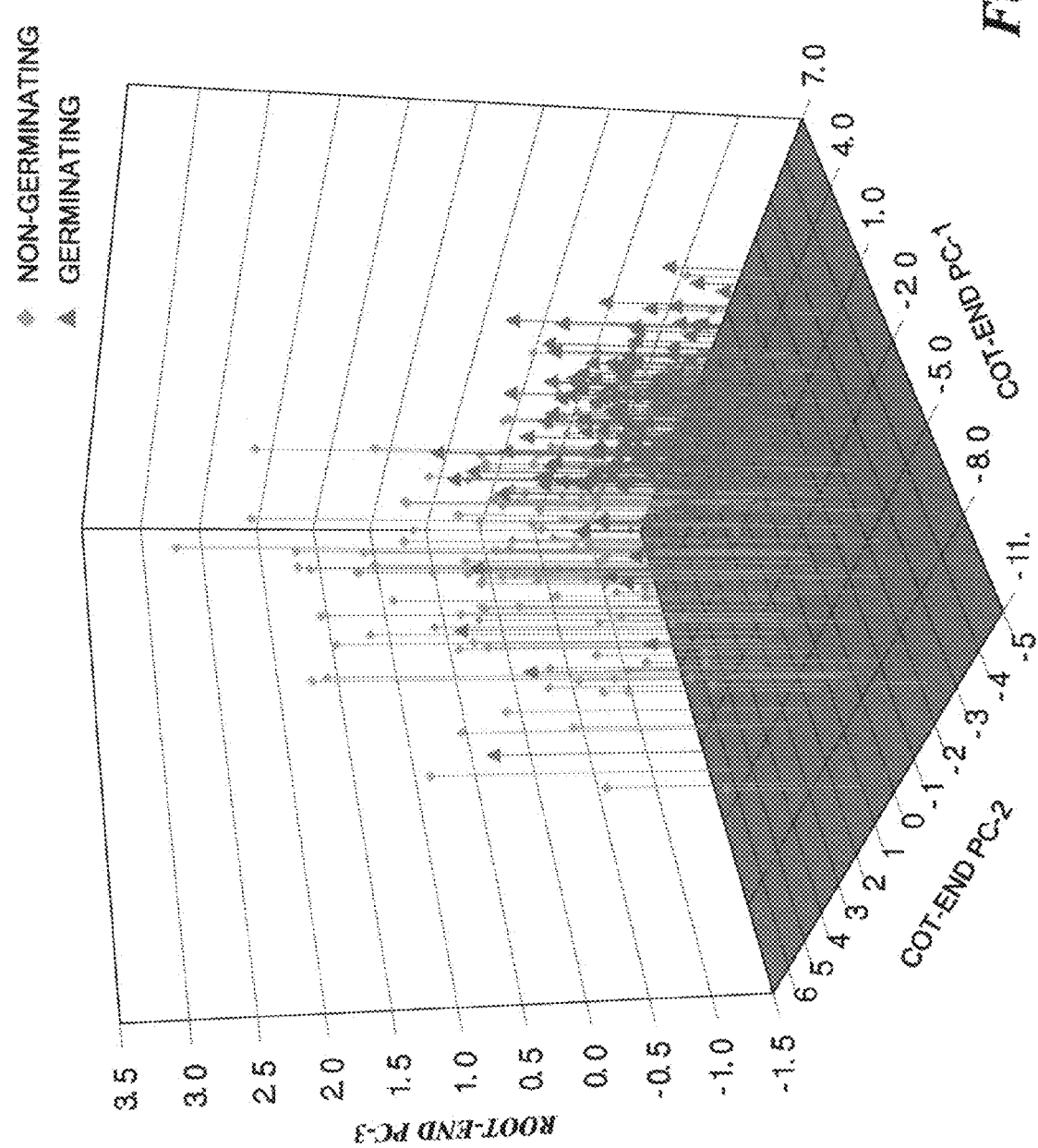
FIG. 10 graphically displays a 3-dimensional score-plot obtained from principal component analysis of spectral data collected using a NIR spectrometer from either the root-end of the embryos (i.e., position 0 to 0.5) or from the cotyledon-end of the embryos (i.e., position 0.5 to 1.0) and plotted with respect to germinating and non-germinating embryos.

Analysis:

The spectrum obtained from the embryos was analyzed with respect to the position from which it was obtained on the embryos. The spectrum of the root-end of the embryos (i.e., from 0 to 0.5), and the spectrum of the cotyledon-end (i.e., from 0.5 to 1.0) were analyzed with respect to whether or not the embryos eventually germinated. A principal component analysis was carried out as described in Example 4. The results are shown in FIG. 10. As shown in FIG. 10, principal components PC-1 and PC-2 5 from the cotyledon end provide a basis to separate embryos that will germinate (arrow heads) from those that won't (diamond heads). As further shown in FIG. 10, the addition of the root-end spectral analysis (PC-3, vertical axis) further separates the embryos that will germinate from those that won't. This analysis would allow one to select a purer population of embryos with high germination potential to pass forward to manufactured seed production. The separating boundary may be defined mathematically as a flat or curved two-dimensional surface positioned to produce a significantly higher germinating population than would be obtained without selection.

In practice, it is preferable to obtain a population with fewer non-germinating embryos, even if it means eliminating some embryos that may germinate because the cost of producing an embryo is much lower than the cost of carrying a non-germinating embryo through manufactured seed processing and into the nursery, only to have it not germinate.

In this Example, the data obtained revealed that it is possible to define simple PC boundaries based on cotyledon-end spectra that would allow for selection of a population of 35 embryos with 100% germination success. When the root-end spectra are added to the cotyledon-end spectra, a population of 57 embryos with a 100% germination success could be selected. Therefore, since these data were only taken from two positions on the embryo, it is expected that the use of multiple positions as with the hyperspectral line imaging analysis methods and systems described herein will allow for increased accuracy and efficiency in selecting embryos with high germination potential for production purposes, such as for insertion into manufactured seed.

Overall Summary:

As described in Example 2, it was determined that the imaging system 300 of the invention with light diffusing sample chamber 400 resulted in a pixel luminance frequency histogram of the reference background (Gore-Tex®) with a peak at approximately 1000 on a scale of 0 to 4096 grayscale units, which was much improved over the <500 unit peak value and high spatial variation originally obtained using the conventional imaging system 100 described in EXAMPLE 1.

As described in Example 4, hyperspectral line image data was used to distinguish between different types of embryos including zygotic versus somatic embryos, somatic embryos of different genotypes, and somatic embryos of the same genotype that were produced using different culture conditions.

As described in Example 5, the use of wavelength-by-position data obtained from hyperspectral line imaging of embryos allowed for an increased accuracy in classification of embryos in comparison to the use of wavelength data alone.

Finally, as described in the present Example, it is demonstrated that wavelength-by-position data obtained from the cotyledonary-end and the root-end of embryos allows for increased accuracy in selecting embryos with high germination potential.

Taken together, these data demonstrate that embryos can be accurately classified and separated by their NIR wavelength-by-position characteristics into embryo types, including embryos of high germination potential.

While the preferred embodiment of the invention has been illustrated and described, it will be appreciated that various changes can be made therein without departing from the spirit and scope of the invention.

While illustrative embodiments have been illustrated and described, it will be appreciated that various changes can be made therein without departing from the spirit and scope of the invention.

The embodiment of the invention in which an exclusive property or privilege is claimed are defined as follows:

1. A method for classifying plant embryos comprising:
   (a) developing a classification model by
      (i) acquiring reflectance spectral raw data representative of a known embryo type by obtaining a plurality of line images of a plurality of embryos of the known embryo type, wherein the plurality of line images are taken from a plurality of positions along and substantially perpendicular to a desired axis of ones of the plurality of embryos;
      (ii) performing a data analysis by applying one or more classification algorithms to the spectral raw data, the data analysis resulting in development of a classification model for classifying plant embryos by embryo type;
   (b) acquiring, by a computer, reflectance spectral raw data of a plant embryo of unknown embryo type by obtaining a plurality of line images of the plant embryo of unknown embryo type, wherein the plurality of line images are taken from a plurality of positions along and substantially perpendicular to a corresponding axis of the plant embryo of unknown embryo type; and
   (c) applying the developed classification model to the spectral raw data of the plant embryo of unknown embryo type in order to classify the type of plant embryo of unknown embryo type.

2. The method of claim 1, wherein the plant embryo of unknown embryo type is classified based on a quantifiable feature selected from the group consisting of a morphological feature, a zygotic embryo, a somatic genotype, or embryo conversion potential.

3. The method of claim 1, wherein the spectral raw data of the plant embryo of unknown embryo type is obtained from at least 5 positions along the corresponding axis of the embryo of unknown embryo type.

4. The method of claim 1, wherein the corresponding axis of the plant embryo of unknown embryo type is a longitudinal axis of the plant embryo of unknown embryo type.

5. The method of claim 4, wherein the plurality of positions consists of the range from position 0.3 to position 0.9 along the longitudinal axis of the plant embryo of unknown embryo type;
   wherein the embryo of the plant embryo of unknown embryo type has a root cap and a cotyledon tip; and
   wherein the root cap represents position 0 and the cotyledon tip represents position 1.0.

6. The method of claim 1, wherein the each of the plurality of line images of the plant embryo of unknown embryo type is captured as a single pixel by a two-dimensional image sensor.

7. The method of claim 6, wherein the two-dimensional image sensor is configured to capture wavelengths between about 900 and 1680 nm.

8. The method of claim 1, wherein the plurality of line images of the plant embryo of unknown embryo type is output as wavelength-by-position data to at least one of a computer storage device, computer-readable media, or a user interface.

9. The method of claim 1, wherein the plant embryo of unknown embryo type is from a conifer.

10. A method for classifying a plant embryo of an unknown type based on near infrared spectroscopy imaging comprising:
   (a) illuminating an axis of a plant embryo of unknown type;
   (b) capturing a plurality of hyperspectral line images from the light reflected off the illuminated plant embryo, wherein the plurality of hyperspectral line images are captured from a plurality of positions along and substantially perpendicular to the axis of the plant embryo of unknown embryo type;
   (c) splitting the infrared portion of the captured plurality of hyperspectral line images into component wavelengths from 900 to 1680 nm;
   (d) detecting the split line images with a detector array;
   (e) outputting the detected images as wavelength-by-position data of the plant embryo of unknown type to at least one of a computer storage device, computer-readable media, or a user interface; and
   (f) comparing the wavelength-by-position data of the plant embryo of unknown type to wavelength-by-position data of a reference plant embryo of known type to classify the plant embryo.

11. The method of claim 10, wherein the illuminated axis is a longitudinal axis of the plant embryo.

12. The method of claim 10, wherein the plant embryo is from a conifer.

13. The method of claim 10, wherein the plant embryo type is classified based on a quantifiable feature selected from the group consisting of a morphological feature, a zygotic embryo, a somatic genotype, or embryo conversion potential.

* * * * *